(12) United States Patent
Jung et al.

(10) Patent No.: US 8,545,741 B2
(45) Date of Patent: Oct. 1, 2013

(54) METHOD OF MANUFACTURING MICROSTRUCTURE

(75) Inventors: Hyung-Il Jung, Seoul (KR); Do-Hyeon Jeong, Seoul (KR); Kwang Lee, Seoul (KR); Jung-Dong Kim, Seoul (KR); Miroo Kim, Seoul (KR)

(73) Assignee: Nurim Wellness Co. Ltd., Seoul (KR)

( * ) Notice: Subject to any disclaimer, the term of this patent is extended or adjusted under 35 U.S.C. 154(b) by 256 days.

(21) Appl. No.: 13/078,874

(22) Filed: Apr. 1, 2011

(65) Prior Publication Data

US 2011/0240201 A1 Oct. 6, 2011

(30) Foreign Application Priority Data

Apr. 1, 2010 (KR) .................. 10-2010-0030127
Dec. 17, 2010 (KR) .................. 10-2010-0130169

(51) Int. Cl.
*B05D 1/36* (2006.01)
*A61M 5/158* (2006.01)

(52) U.S. Cl.
USPC .......... 264/163; 156/60; 427/372.2; 427/261; 427/289; 427/2.1

(58) Field of Classification Search
USPC ............... 264/163; 156/60; 427/372.2, 261, 427/289, 2.1
See application file for complete search history.

(56) References Cited

U.S. PATENT DOCUMENTS

| 2008/0108959 A1* | 5/2008 | Jung et al. | 604/272 |
| 2009/0053472 A1* | 2/2009 | Spatz et al. | 428/156 |
| 2009/0163881 A1* | 6/2009 | Jung et al. | 604/265 |

FOREIGN PATENT DOCUMENTS

| KR | 10-0793615 B1 | 1/2008 |
| KR | 10-2009-0059971 A | 6/2009 |
| KR | 10-2009-0131540 A | 12/2009 |
| KR | 10-2010-0038071 A | 4/2010 |

* cited by examiner

*Primary Examiner* — Robert J Grun
(74) *Attorney, Agent, or Firm* — Edwards Wildman Palmer LLP; Kongsik Kim

(57) ABSTRACT

Provided are methods of manufacturing microstructures, in which at least one viscous composition each containing at least one active ingredient is disposed directly or indirectly on a first substrate and/or a second substrate and the viscous composition(s) is elongated between the first and second substrates. The methods are simpler and more cost-effective.

17 Claims, 18 Drawing Sheets

FIG. 3
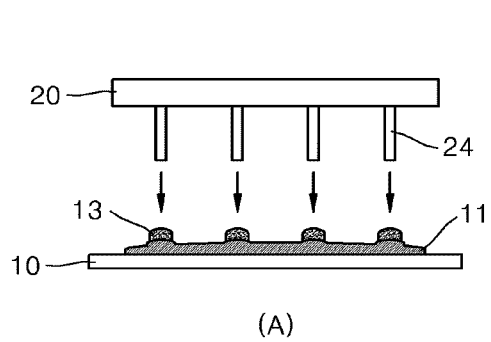
(A)
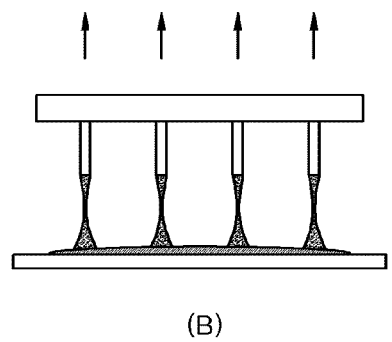
(B)
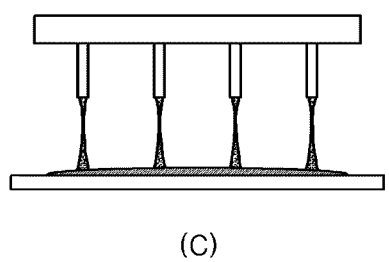
(C)
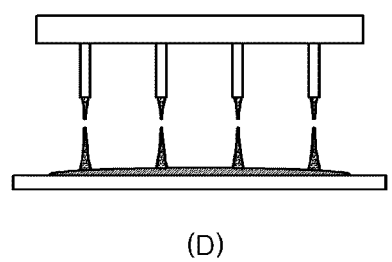
(D)
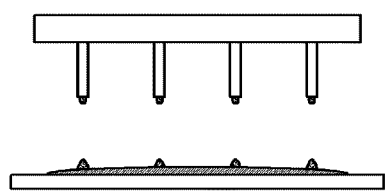
(E)
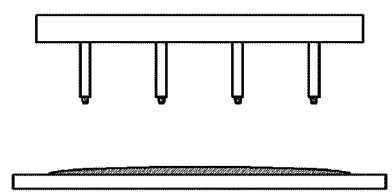
(F)

FIG. 5
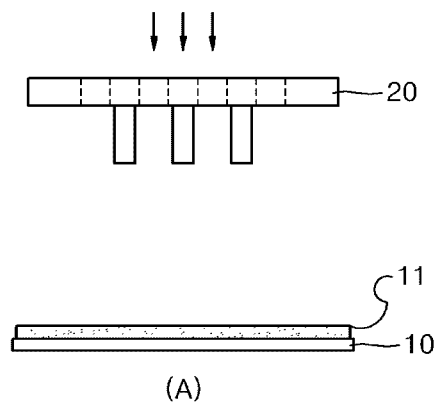
(A)
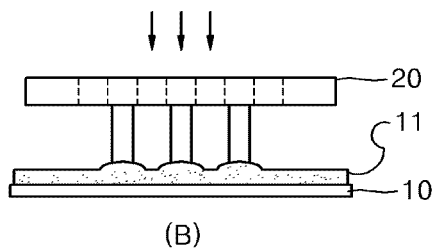
(B)
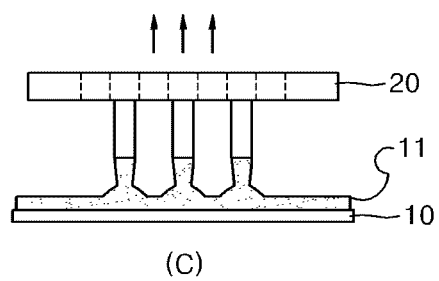
(C)
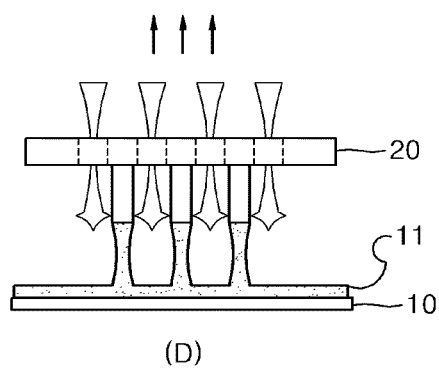
(D)
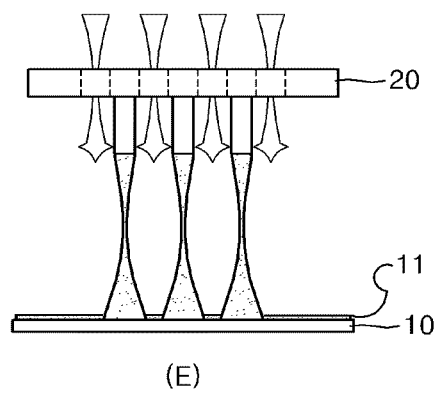
(E)
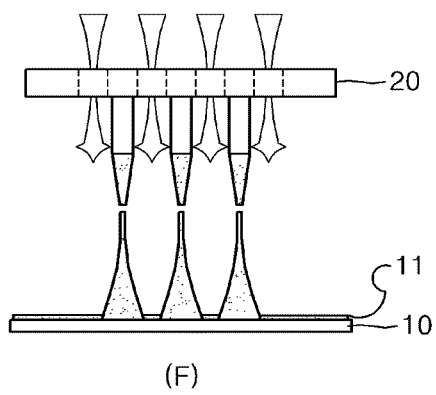
(F)

FIG. 11
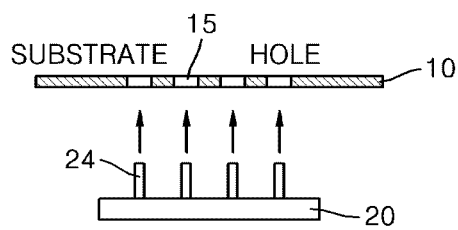
(A)
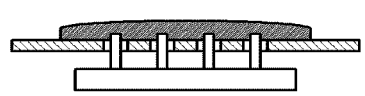
(B)
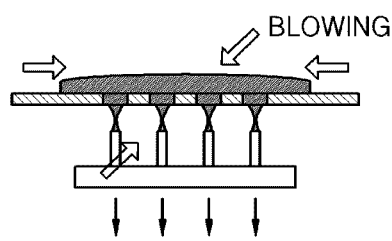
(C)
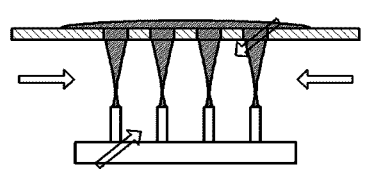
(D)
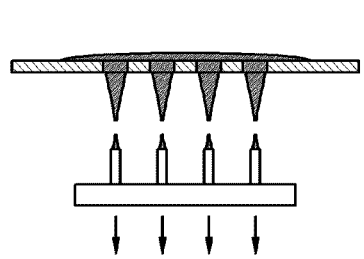
(E)
(F)
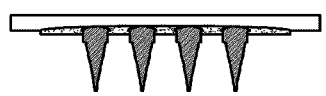
(G)

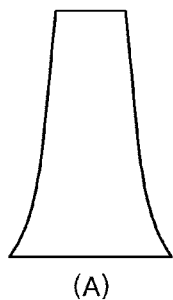
(A)
THIRD EMBODIMENT
LIFTING SPEED:
0.2mm/min

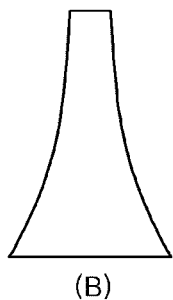
(B)
THIRD EMBODIMENT
LIFTING SPEED:
0.4mm/min

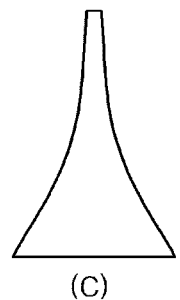
(C)
THIRD EMBODIMENT
LIFTING SPEED:
0.6mm/min

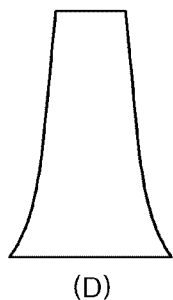
(D)
FIRST EMBODIMENT
DESCENDING SPEED:
0.2mm/min

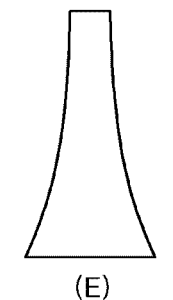
(E)
FIRST EMBODIMENT
DESCENDING SPEED:
0.4mm/min

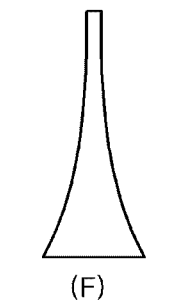
(F)
FIRST EMBODIMENT
DESCENDING SPEED:
0.6mm/min

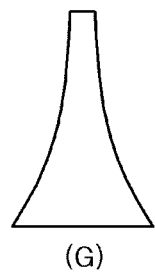
(G)
THIRD
EMBODIMENT
WIND SPEED :
2.4m/s

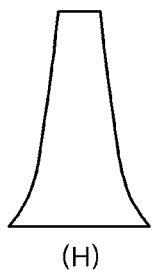
(H)
THIRD
EMBODIMENT
WIND SPEED :
7.2m/s

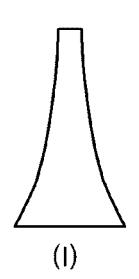
(I)
FIRST
EMBODIMENT
WIND SPEED :
2.4m/s

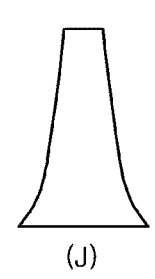
(J)
FIRST
EMBODIMENT
WIND SPEED :
7.2m/s (A)  (B)

METHOD OF MANUFACTURING MICROSTRUCTURE

CROSS-REFERENCE TO RELATED APPLICATION

This application claims priority to and the benefit of Korean Patent Application No. 10-2010-0030127, filed on Apr. 1, 2010 and Korean Patent Application No. 10-2010-0130169, filed on Dec. 17, 2010, which applications are incorporated herein by reference in their entirety.

BACKGROUND

1. Technical Field

The present disclosure relates to a method of manufacturing a microstructure to be used for delivery of an active ingredient(s) to humans or animals.

2. Related Art

Many techniques for delivering one or more active ingredients such as a pharmaceutical, nutritional, or cosmetic compound or composition thereof to humans or animals were proposed. Most common routes of delivery include non-invasive peroral (through the mouth), topical (skin), transmucosal (nasal, buccal/sublingual, vaginal, ocular and rectal), and inhalation routes. Some active ingredients, however, cannot be delivered using these routes because they are susceptible to enzymatic degradation or cannot be absorbed into humans or animals due to some reasons such as molecular size and charge issues. For thses and other reasons, some active ingredients are or have to be delivered by injection.

A conventional needle has been used for injection delivery. This transdermal needle delivery techniques, however, have some problems. For example, the techniques may cause the humans or animals subjected to the injection to feel pain and a skin thereof to be damaged, and/or may cause bleeding and/or infection in the injected area.

To solve these problems, injection techniques by using microneedles have been proposed. Advantages of the transdermal microneedle delivery techniques are, for example, that they are noninvasive, safe, hygienic, and user friendly. The microneedles are required to have some properties such as, e.g., sufficient fineness, sufficient length, and sufficient hardness for efficient delivery. More specifically, in case of a human subject, to deliver active ingredients without causing pain to a specific layer of a skin of the subject, which is composed of stratum corneum (<20 pm), epidermis (<100 μm), and dermis (300 to 2,500 μm), the microneedles need to have a top diameter of approximately 30 μm, an effective length of 200 to 2,000 μm, and a sufficient hardness. In addition, to deliver active ingredients by biodegradable microneedles, any process that can degrade the activities of the active ingredients must be avoided, examples of which process may include a high heat treatment, an organic solvent treatment, and the like.

Methods for manufacturing a microstructure (e.g., a microstructure in which microneedles are provided) were proposed, as disclosed in, e.g., Biodegradable Polymer Microneedles: Fabrication, Mechanics and Transdermal Drug Delivery, *Journal of Controlled Release* 104, 2005, 5166; Polymer Microneedles for Controlled-Release Drug Delivery, *Pharmaceutical Research* 23, 2006, 1008; Japanese Patent Application Publication No. 2005154321; Sugar Micro Needles as Transdermic Drug Delivery System, *Biomedical Microdevices* 7, 2005, 185; Minimally Invasive Protein Delivery with Rapidly Dissolving Polymer Microneedles, *Advanced Materials* 2008, 1; Dissolving Microneedles for Transdermal Drug Delivery, *Biomaterials* 2007, 1; and U.S. Patent Application Publication No. 20080157421 A1.

Some of the methods, however, do not provide a microstructure having microneedles that have sufficient (top) diameter, sufficient length, and sufficient hardness and some of the methods involve degradation of the activity of active ingredients. Thus, there is still a need for a method for manufacturing a microstructure having desired properties in a simpler and more cost-effective way.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

A first embodiment of the present invention provides a method of manufacturing a microstructure, the method comprising the steps of: (a) facing the inner surface of a first substrate with the inner surface of a second substrate, wherein the first substrate has a first viscous composition formed directly or indirectly on the inner surface of the first substrate; (b) moving the first substrate, the second substrate, or both so as to allow the first viscous composition and the second substrate to become in contact with each other; (c) moving the first substrate, the second substrate, or both so as to allow the first viscous composition to be elongated; (d) solidifying the elongated first viscous composition; and (e) cutting the solidified first viscous composition at predetermined positions between the first substrate and the second substrate to provide a microstructure. A modified embodiment thereof provides a method manufacturing a microstructure, the method comprising the steps of: (a) facing the inner surface of a first substrate with the inner surface of a second substrate, wherein the first substrate has a first viscous composition formed directly or indirectly on the inner surface of the first substrate; (b) moving the first substrate, the second substrate, or both at a first speed so as to allow the first viscous composition and the second substrate to become in contact with each other; (c) blowing air directly or indirectly to the first viscous composition to solidify the first viscous composition; and (d) moving the first substrate, the second substrate, or both at a second speed higher than the first speed so as to cut the solidified first viscous composition.

A second embodiment of the present invention provides method of manufacturing a microstructure, the method comprising the steps of: (a) facing the inner surface of a first substrate with the inner surface of a second substrate, wherein the first substrate has a first viscous composition spotted directly or indirectly on the inner surface of the first substrate at predetermined positions and the second substrate has a second viscous composition spotted directly or indirectly on the inner surface of the second substrate at predetermined positions; (b) moving the first substrate, the second substrate, or both so as to allow the first viscous composition and the second viscous composition to become in contact with each other; (c) moving the first substrate, the second substrate, or both so as to allow the first viscous composition and the second viscous composition to be elongated; (d) solidifying the elongated first and second viscous compositions; and (e) cutting the solidified first and second viscous compositions at predetermined positions between the first substrate and the second substrate to provide a microstructure. A modified embodiment thereof provides a method of manufacturing a microstructure, the method comprising the steps of: (a) facing the inner surface of a first substrate with the inner surface of a second substrate, wherein the first substrate has a first viscous composition spotted directly or indirectly on the inner surface of the first substrate at predetermined positions and the second substrate has a second viscous composition spotted directly or indirectly on the inner surface of the second substrate at predetermined positions; (b) moving the first substrate, the second substrate, or both at a first speed so as to allow the first viscous composition and the second viscous composition to become in contact with each other; (c) blowing air directly or indirectly to the first and second viscous compositions to solidify the first and second viscous compositions; and (d) moving the first substrate, the second substrate, or both at a second speed higher than the first speed so as to cut the solidified first and second viscous compositions.

A third embodiment of the present invention provides a method of manufacturing a microstructure, the method comprising the steps of: (a) facing the inner surface of a first substrate with the inner surface of a second substrate, wherein the first substrate has a plurality of through holes and the second substrate has a plurality of contact protrusions each protruding by a predetermined length from the inner surface of the second substrate; (b) forming a first viscous composition directly or indirectly on the outer surface of the first substrate; (c) moving the first substrate, the second substrate, or both so that the contact protrusions are inserted into the through holes thereby allowing the first viscous composition and the contact protrusions to become in contact with each other; (d) moving the first substrate, the second substrate, or both so as to allow the first viscous composition to be elongated; (e) solidifying the elongated first viscous composition; and (f) cutting the solidified first viscous composition at predetermined positions between the first substrate and the second substrate to provide a microstructure. A modified embodiment thereof provides a method of manufacturing a microstructure, the method comprising the steps of: (a) facing the inner surface of a first substrate with the inner surface of a second substrate, wherein the first substrate has a plurality of through holes and the second substrate has a plurality of contact protrusions each protruding by a predetermined length from the inner surface of the second substrate; (b) forming a first viscous composition directly or indirectly on the outer surface of the first substrate; (c) moving the first substrate, the second substrate, or both at a first speed so that the contact protrusions are inserted into the through holes thereby allowing the first viscous composition and the contact protrusions to become in contact with each other; (d) moving the first substrate, the second substrate, or both so as to allow the first viscous composition to be elongated to a predetermined length; (e) blowing air directly or indirectly to the first viscous composition to solidify the first viscous composition; and (f) moving the first substrate, the second substrate, or both at a second speed higher than the first speed so as to cut the solidified first viscous composition.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 3 is a diagram illustrating still another example of the method for manufacturing a microstructure according to the first embodiment of the present invention;

FIG. 5 is a diagram illustrating a further example of the method for manufacturing a microstructure according to the first embodiment of the present invention;

FIG. 11 is a diagram illustrating an example of the method for manufacturing a microstructure according to the third embodiment of the present invention;

FIGS. 16A to 16J are schematic diagrams showing various shapes of microstructures manufactured by the methods for manufacturing a microstructure according to the first, second, and third embodiments of the present invention;

DETAILED DESCRIPTION OF EXEMPLARY EMBODIMENTS

Figure 1:
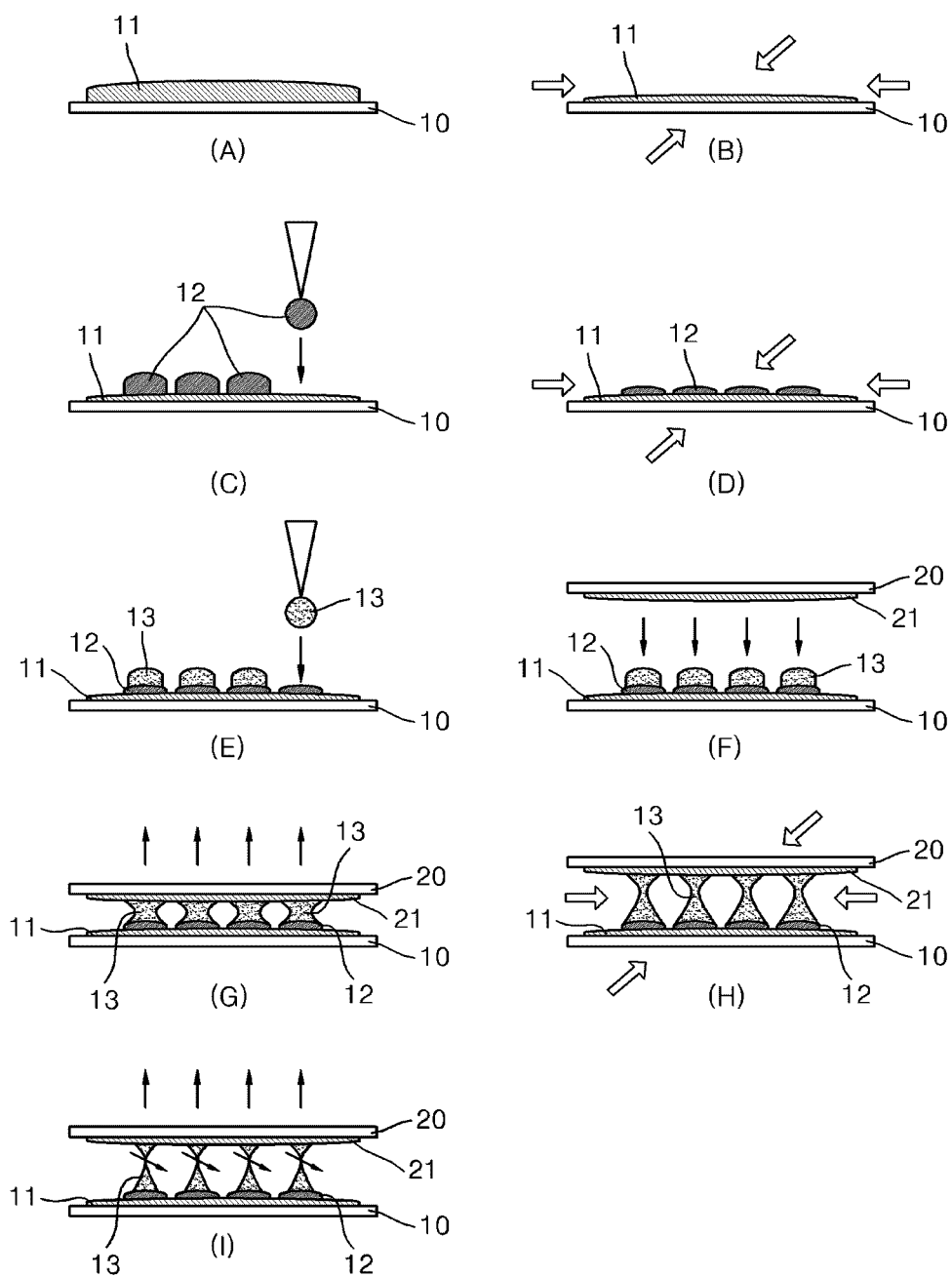
FIG. 1 is a diagram illustrating an example of the method for manufacturing a microstructure according to the first embodiment of the present invention.
Figure 2:
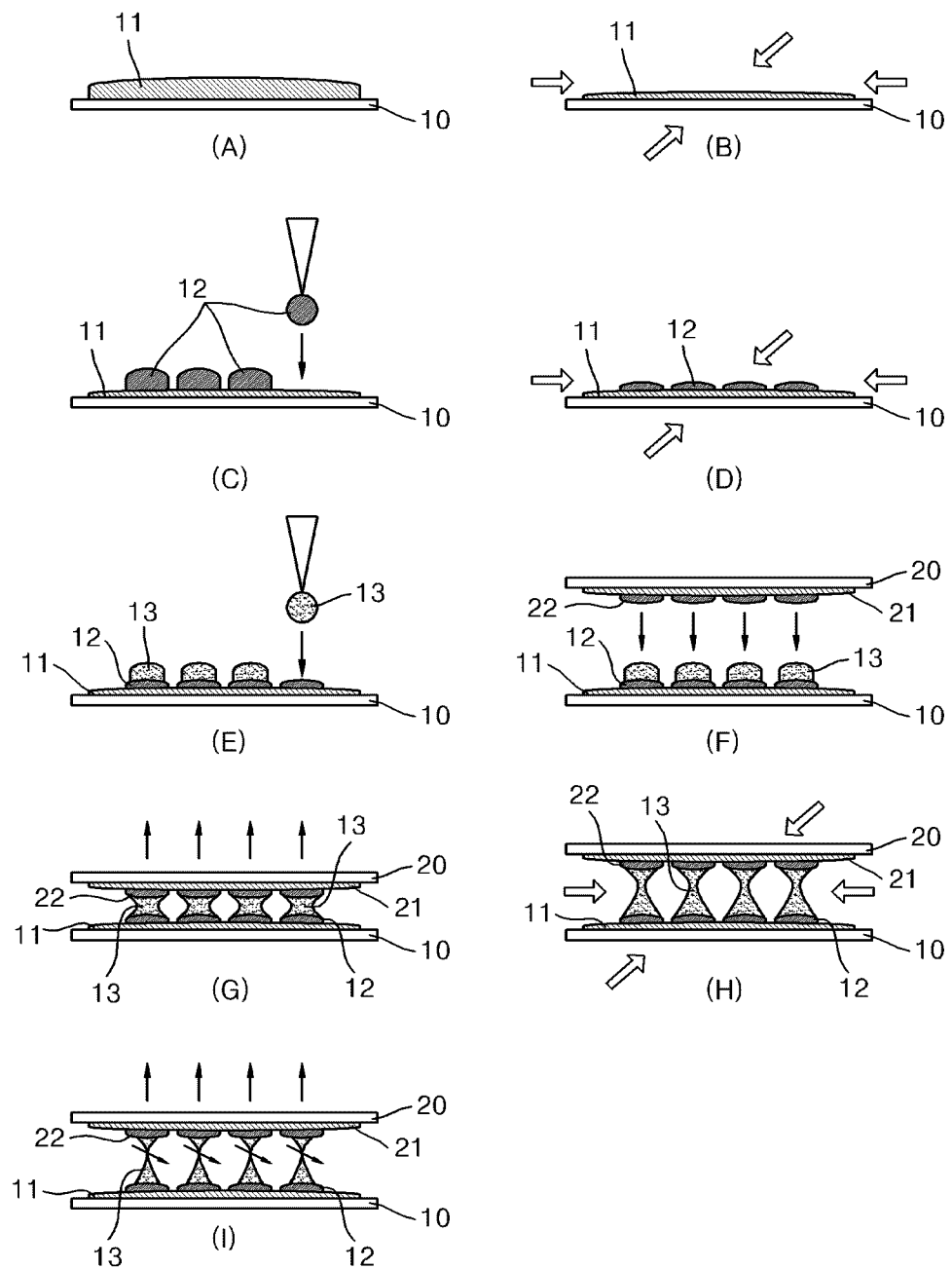
FIG. 2 is a diagram illustrating another example of the method for manufacturing a microstructure according to the first embodiment of the present invention.
Figure 4:
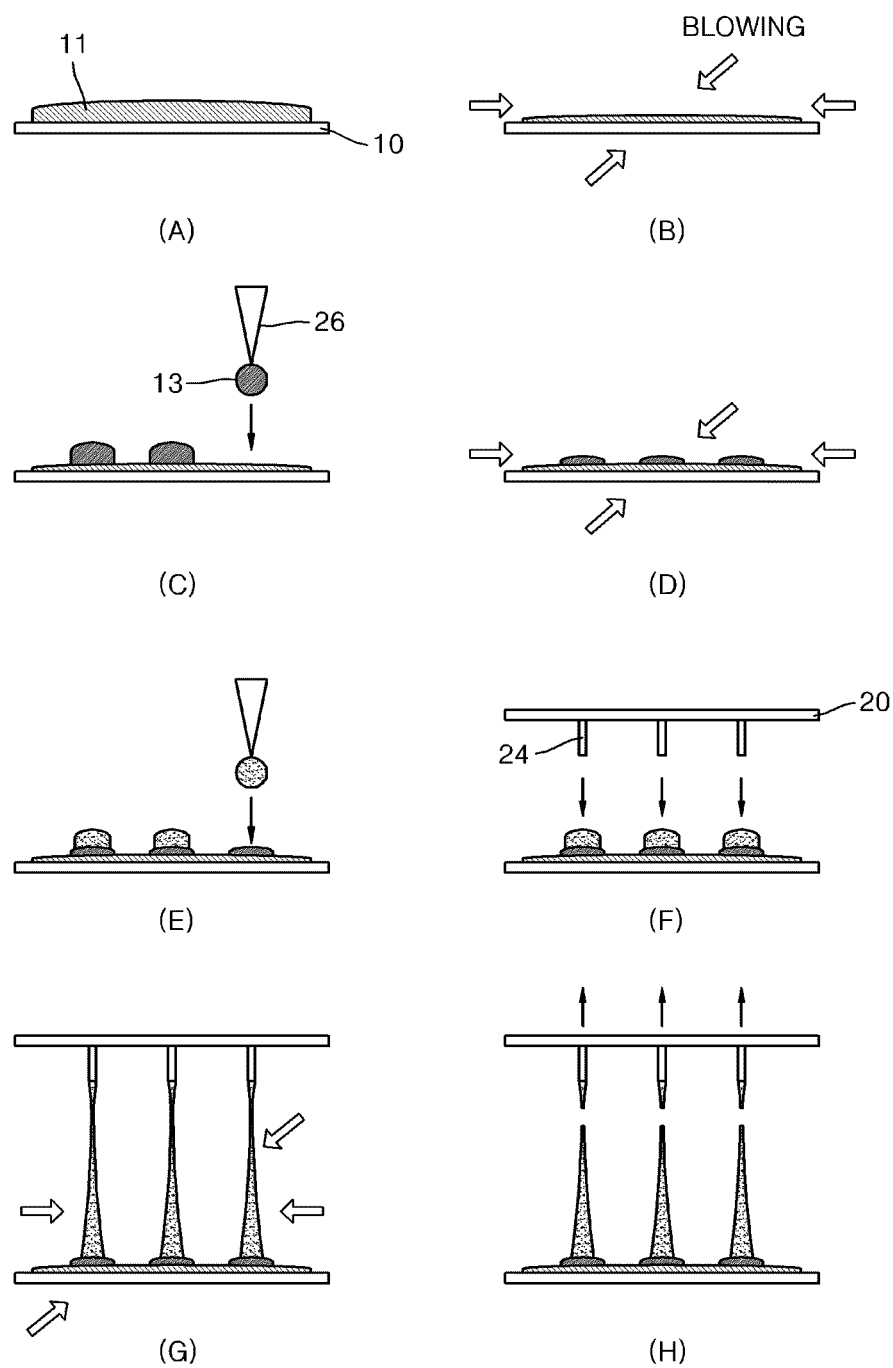
FIG. 4 is a diagram illustrating still yet another example of the method for manufacturing a microstructure according to the first embodiment of the present invention.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

First Embodiment

Referring to FIGS. 1 to 5, the method of manufacturing a microstructure according to the first embodiment comprises the steps of: (a) facing the inner surface of a first substrate 10 with the inner surface of a second substrate 20, wherein the first substrate 10 has a first viscous composition 13 formed directly or indirectly on the inner surface of the first substrate 10; (b) moving the first substrate 10, the second substrate 20, or both so as to allow the first viscous composition 13 and the second substrate 20 to become in contact with each other; (c) moving the first substrate, the second substrate, or both so as to allow the first viscous composition 13 to be elongated; (d) solidifying the elongated first viscous composition 13; and (e) cutting the solidified first viscous composition 13 at predetermined positions between the first substrate 10 and the second substrate 20 to provide a microstructure.

Suitably, at least one of the steps (a) to (e) may be performed while air is blown. Air can be blown in many ways. For example, it can be blown directly or indirectly and/or continuously or intermittently toward the viscous composition 13. Also, for example, it can be blown in symmetrical directions, such as two directions or four directions. Also, it can be blown between two of the steps (e.g., between (a) and (b). In the drawings, the block arrows represent the direction of air blown while solid arrows represent the direction of movement of an object such as the substrates, viscous materials, viscous compositions, etc. The method, however, may be performed without air blowing as shown in FIG. 3.

The term "viscous composition" used herein refers to a composition that contains a viscous material and can be elongated by movement of the first substrate 10, and the second substrate 20, or both. The viscosity of a viscous composition may be appropriately adjusted by changing the kinds, concentrations, and temperature of a viscous material and other materials contained in the viscous composition or by adding a viscosity modifier. Although the viscosity of the viscous composition is not limited to a particular value, a preferable range of the viscosity for the purpose of the present invention is 200,000 cSt or less.

Preferably, an example of the viscous material that can be contained in the viscous composition and used as the first to fourth viscous materials in the present invention is a cellulose polymer such as, e.g., hydroxypropyl methylcellulose, hydroxyalkyl cellulose (preferably, hydroxyethyl cellulose or hydroxypropyl cellulose), ethyl hydroxyethyl cellulose, alkyl cellulose, and carboxymethylcellulose. In an embodiment of the present invention, first to fourth viscous materials used for forming first and second top/bottom layers and first and second viscous compositions, which will be detained below, may be prepared by using the same material. In another embodiment, they may be prepared by using different materials.

Non-limiting examples of the viscosity modifier may include hyaluronic acid and salts thereof, polyvinylpyrrolidone (PVP), cellulose polymer, dextran, gelatin, glycerin, polyethylene glycol, polysorbate, propylene glycol, povidone, carbomer, gum ghatti, guar gum, glucomannan, glucosamine, dammer resin, rennet casein, locust bean gum, microfibrillated cellulose, psyllium seedgum, xanthan gum, arabino galactan, gum arabic, alginic acid, gelatin, gellan gum, carrageenan, karaya gum, curdlan, chitosan, chitin, tara gum, tamarind gum, tragacanthgum, furcelleran, pectin, or pullulan.

Figure 8:
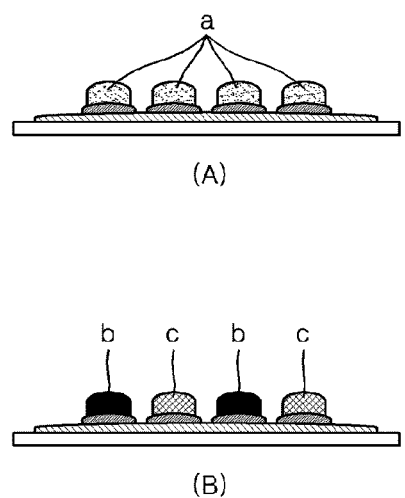
FIG. 8A shows a first substrate having a viscous composition (a) formed thereon and FIG. 8B shows a first substrate having two different viscous compositions (b, c) formed thereon according to the first, second, and third embodiments of the present invention.
Figure 13:
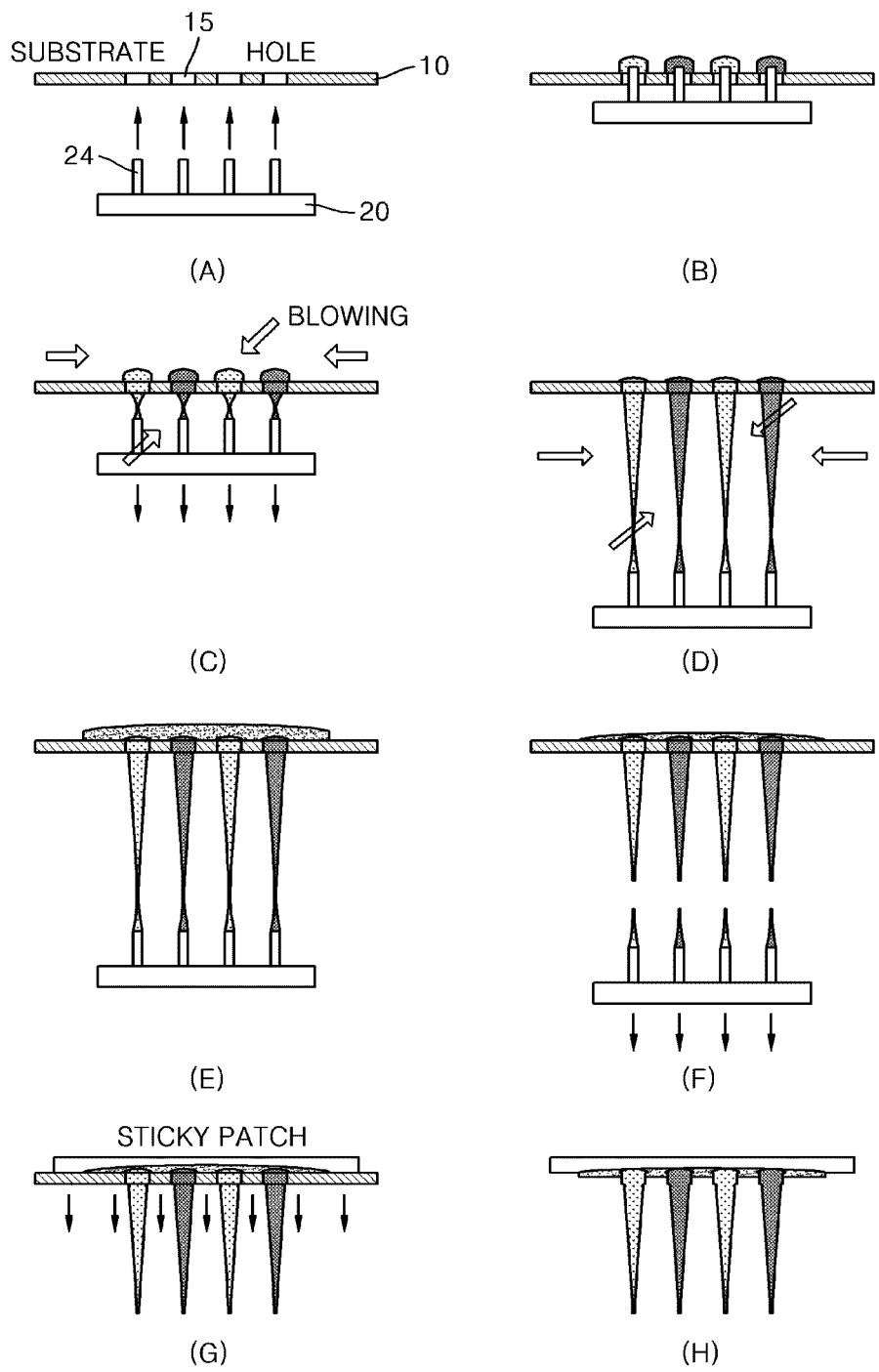
FIG. 13 is a diagram illustrating still another example of the method for manufacturing a microstructure according to the third embodiment of the present invention.

Preferably, the viscous composition may contain only a viscous material. Also preferably, the viscous composition may further contain at least one active ingredient that can induce a pharmacological or cosmetic effect if it is when being introduced into a subject, as shown in FIGS. 8 and 13. The viscous composition may further contain at least one biocompatible material and/or a biodegradable material. The term "biocompatible material" refers to a material that is substantially non-toxic in a human body, chemically inactive, and deficient in immunogenicity. The term "biodegradable material" refers to a material that is degradable by body fluids or microorganisms in living bodies. The biocompatible or biodegradable material serves as a skeletal material of microstructures according to the present invention.

Non-limiting examples of the biocompatible material and/or biodegradable material may include polyester, polyhydroxyalkanoates (PHAs), poly(α-hydroxy acid), poly(β-hydroxy acid), poly(3-hydroxybutyrate-co-valerate) (PHBV), poly(3-hydroxy proprionate) (PHP), poly(3-hydroxyhexanoate) (PHH), poly(4-hydroxy acid), poly(4-hydroxybutyrate), poly(4-hydroxyvalerate), poly(4-hydroxyhexanoate), poly(ester amide), polycaprolactone, polylactide, polyglycolide, poly(lactide-co-glycolide) (PLGA), polydioxanone, poly(ortho ester), polyetherester, polyanhydride, poly(glycolic acid-co-trimethylene carbonate), polyphosphoester (PPE), PPE urethane, poly(amino acid), polycyanoacrylate, poly(trimethylene carbonate), poly(iminocarbonate), poly(tyrosine carbonate), polycarbonate (PC), poly (tyrosine arylate), polyalkylene oxalate, polyphosphazene, PHA-PEG, ethylenevinyl alcohol copolymer (EVOH), polyurethane, silicon, polyester, polyolefin, polyisobutylene-ethylene-α-olefin copolymer, stylene-isobutylene-stylene triblockcopolymer, acryl polymers and copolymers, vinyl halide polymers and copolymers, polyvinyl chloride, polyvinyl ether, polyvinyl methylether, polyvinylidene halide, polyvinylidene fluoride, polyvinylidene chloride, polyfluoroalken, polyperfluoroalken, polyacrylonitrile, polyvinyl ketone, polyvinyl aromatics, polystyrene, polyvinyl ester, polyvinyl acetate, ethylene-methyl methacrylate copolymers, acrylonitrile-stylene copolymer, ABS resin-ethylenevinyl acetate copolymer, polyamide, alkyde resin, polyoxymethylene, polyimide, polyether, polyacrylate, polymethacrylate, polyacrylic acid-co-maleic acid, chitosan, dextran, cellulose, heparin, hyaluronic acid, alginate, inulin, starch, and glycogen.

The biocompatible material or biodegradable material has a certain level of viscosity when it is dissolved in a solvent. Examples of the solvent may include, but not limited to, water, absolute or hydrous lower alcohol having 1 to 4 carbon atoms, acetone, ethyl acetate, chloroform, 1,3-butylene glycol, hexane, diethyl ether, and butylacetate.

The viscous composition may further contain at least one active ingredient. The term "active ingredient" used herein refers to an ingredient that can induce a pharmacological or cosmetic effect when being introduced into a subject including a human. The active ingredient used in the present invention may include, for example, chemical drugs, protein medicines, peptide medicines, or hexane molecules and nanoparticles for gene therapy. Non-limiting examples of the active ingredient may include anti-inflammatory agents, anodynes, antiarthritics, spasmolytics, antidepressants, antipsychotic drugs, tranquilizers, antianxiety drugs, narcotic antagonists, anti-Parkinson's disease drugs, cholinergic agonists, anticancer drugs, angiogenesis inhibitors, immunosuppressants, antiviral agents, antibiotics, anorectic agents, anodynes, anticholinergics, antihistamines, antimigraine drugs, hormone drugs, coronary, cerebrovascular, or peripheral vascular vasodilators, contraceptives, antithrombotic drugs, diuretics, antihypertensive drugs, remedies for cardiovascular disease, or cosmetic ingredients (e.g., a wrinkle enhancer, a skin-aging inhibitor, or skin whitener).

As described below, the methods according to the present invention can be performed without heat treatment. Accordingly, the methods can be applied to a heat-vulnerable active ingredient such as, e.g., a protein medicine, a peptide medicine, a vitamin, and hexane molecules. Examples of the protein medicine and peptide medicine may include, but not limited to, hormones, hormone agonists, enzymes, enzyme inhibitors, signal transduction proteins or portions thereof, antibodies or portions thereof, single-chain antibodies, binding proteins or binding domains thereof, antigens, adhesion proteins, structural proteins, regulatory proteins, toxin proteins, cytokines, transcription factors, blood coagulation factors, or vaccines. More specifically, the protein and peptide medicines may include insulin, insulin-like growthfactor 1 (IGF-1), growth hormones, erythropoietin, granulocyte-colony-stimulating factors (G-CSFs), granulocyte/macrophage-colony-stimulating factors (GM-CSFs), interperon-alpha($\alpha$), interperon-beta($\beta$), interperon-gamma($\gamma$), interleukin-1($\alpha$ and ($\beta$), interleukin-3, interleukin-4, interleukin-6, interleukin-2, epidermal growth factors (EGFs), calcitonin, adrenocorticotropic hormone (ACTH), tumor necrosis factors (TNFs), atobisban, buserelin, cetrorelix, deslorelin, desmopressin, dynorphin A (1-13), elcatonin, eleidosin, eptifibatide, growth hormone releasing hormone-II (GHRH-II), gonadorelin, goserelin, histrelin, leuprorelin, lypressin, octreotide, oxytocin, pitressin, secretin, sincalide, terlipressin, thymopentin), thymosine $\alpha$1, triptorelin, bivalirudin, carbetocin, cyclosporin, exedine, lanreotide, luteinizinghormone-releasing hormone (LHRH), nafarelin, parathormone, pramlintide, enfuvirtide (T-20), thymalfasin, and ziconotide.

Figure 9:
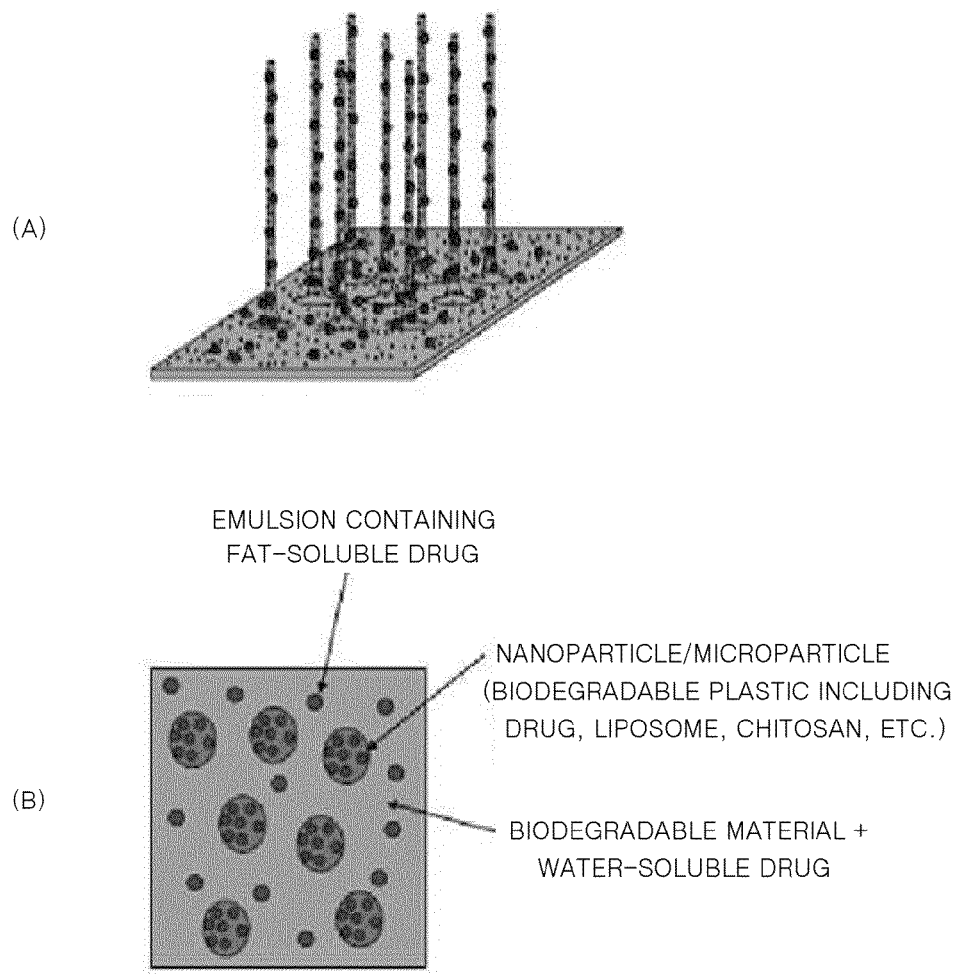
FIGS. 9A and 9B show examples of a microstructure manufactured according to the first, second, and third embodiments of the present invention, in which an active ingredient (e.g., drug) and other substances are included.

Preferably, the active ingredient may be incorporated into various forms such as microparticles, nanoparticles, emulsion, or any combination thereof. The incorporated active ingredient can be mixed with the biocompatible or biodegradable material serving as the skeletal material of the microstructure. Accordingly, microstructures manufactured by the methods of the present invention may contain microparticles, nanoparticles, emulsions, or any combination thereof, as shown in FIG. 9.

An active ingredient carried in the form of microparticles or nanoparticles can be mixed with a biocompatible or biodegradable material by known methods such as, e.g., a multiple emulsion method, a dispersion dry method, and a particle precipitation method. Preferably, the microparticles or nanoparticles may be prepared using polyester, PHAs, poly($\alpha$-hydroxy acid), poly($\beta$3-hydroxy acid), PHBV, PHP, PHH, poly(4-hydroxy acid), poly(4-hydroxybutyrate), poly(4-hydroxyvalerate), poly(4-hydroxyhexanoate), poly(ester amide), polycaprolactone, polylactide (PLA), polyglycolide (PGA), PLGA, polydioxanone, poly(ortho ester), polyanhydride, poly(glycolic acid-co-trimethylene carbonate), PPE, PPE urethane, poly(amino acid), polycyanoacrylate, poly(trimethylene carbonate), poly(iminocarbonate), poly(tyrosine carbonate), PC, poly(tyrosine arylate), polyalkylene oxalate, polyphosphazene, PHA-PEG, PVP, polybutadiene, polyhydroxy butyric acid, polymethyl methacrylate, polymethacrylic acid ester, polypropylene, polystyrene, polyvinylacetal diethylamino acetate, polyvinyl acetate, polyvinyl alcohol (PVA), polyvinylbutyral, polyvinylformal, vinyl chloride-propylene-vinyl acetate copolymer, vinyl chloride-vinyl acetate copolymer, coumarone-indene polymer, dibutylamino hydroxypropyl ether, ethylene-vinyl acetate copolymer, glycerol distearate, 2-methyl-5-vinyl pyridine methacrylate-methacrylic acidcopolymer, hyaluronic acid, myristic acid, palmitic acid, stearic acid, benenic acid, cellulose or derivatives thereof, maltose, dextran, glucomannan, glucosamine, chitosan, heparin, alginate, inulin, starch, glycogen, chitin, chondroitin, dextrin, keratan sulfate, beef tallow, whale wax, beeswax, paraffin wax, or castor wax. More preferably, the microparticles or nanoparticles may be prepared using PLA, PGA, PLGA, cellulose or derivatives thereof, maltose, dextran, glucomannan, glucosamine, chitosan, heparin, alginate, inulin, starch, or glycogen. The material of the microparticles or nanoparticles may be the same as or different from that of the biocompatible or biodegradable material.

An active ingredient can be emulsified in a biocompatible or biodegradable material as water-in-oil (W/O) emulsion, O/W emulsion, or multiple emulsion by known methods. The emulsion can be prepared with or without a natural emulsifier (e.g., lecithin, borax, stearic acid, amisol soft, helio gel, beeswax, xanthan gum, or emulsifying wax), a synthetic emulsifier (e.g., O/W emulsifiers including PEG-8 dilaurate, PEG-150 distearate, PEG-8 stearate, PEG-40 distearate, and PEG-100 distearate and W/O emulsifiers including sorbitan stearate, sorbitan oleate, sorbitan sesquioleate, and sorbitan trioleate), or a combination thereof. For example, a fat-soluble active ingredient may be emulsified in a water-soluble biocompatible or biodegradable material in using a homogenizer.

Preferably, the biocompatible or biodegradable material as a skeletal material of microstructures may further contain an active agent. The active ingredient contained in the biocompatible or biodegradable material, the active ingredient contained in microparticles or nanoparticles, and the active ingredient contained in an emulsion may be designed to be same or different.

As the biocompatible or biodegradable material, the nanoparticles or microparticles, and the emulsion may be decomposed at different times, microstructures manufactured by the methods according to some embodiments of the present invention can provide a timed-release or controlled-release delivery of the active ingredient(s).

Suitably, the viscous composition may further include a form of energy. In this case, microstructures may be used to transmit energy, such as thermal energy, light energy, or electrical energy. For example, in photodynamic therapy, microstructures may induce light toward a specific region of the body of a subject so that the light can directly act on body tissues or work on a medium, such as light-sensitive molecules.

The viscous material or viscous composition, as described below, may be formed on the first substrate 10 and/or the second substrate 20. The first substrate 10 and the second substrate 20 can be made of any material on which the viscous material or viscous composition can be formed. If the first or second substrate is made of a material that exhibits a certain viscosity, the viscous material is not necessary to be formed on the substrate. Non-limiting examples of the material for the first substrate 10 and the second substrate 20 may include a polymer, an organic chemical, a metal, a ceramic, a semiconductor, a glass, polymethylmethacrylate (PMMA) and stainless steel.

According to the first embodiment, the step (a) may, preferably, comprise the steps of: forming a first bottom layer 11 on the first substrate 10 by applying a first viscous material on the inner surface of the first substrate 10 and solidifying the applied first viscous material; and spotting the first viscous composition 13 on the first bottom layer 10.

The first bottom layer 11 may be formed as a continuous layer or a discontinuous layer comprising a plurality of spots spaced apart from each other. In case where the first bottom layer 11 is formed as a discontinuous layer, the first viscous composition 13 may, preferably, be spotted on all or part of the plurality of spots oft the first bottom layer 11.

Figure 6:
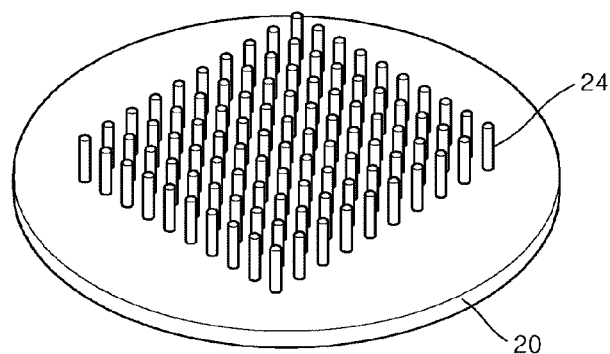
FIG. 6 shows an example of a second substrate that can be used in the methods for manufacturing a microstructure according to the first and third embodiments of the present invention.
Figure 7:
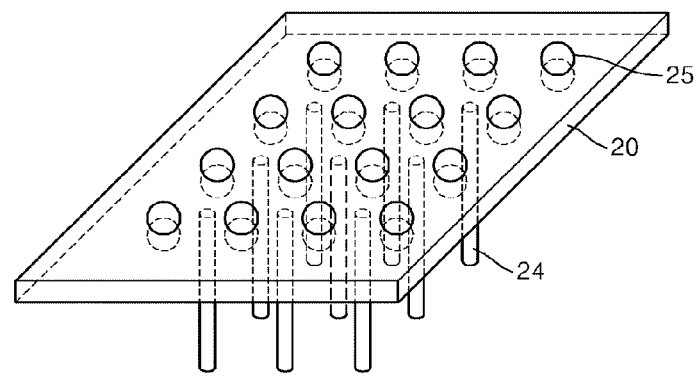
FIG. 7 shows another example of a second substrate that can be used in the methods for manufacturing a microstructure according to the first and third embodiments of the present invention.

The first viscous composition 13 may be formed on the inner surface of the first substrate 10 as a continuous layer or a discontinuous layer. In case where the first viscous composition is formed as a continuous layer, the second substrate 20 may, suitably, have a plurality of contact protrusions 24 each protruding by a predetermined length from the inner surface of the second substrate 20, as shown in FIG. 6. In this case, in the step (b), the contact protrusions 24 may become in contact with the first viscous composition 13. Preferably, the second substrate 20 may have a plurality of through holes 25, as shown in FIG. 7. Air can be blown through at least one of the through holes 25 in at least one of the steps (a) to (e). Preferably, the distance between the centers of any two of the through holes 25 may be set to be equal to the distance between the centers of any two of the contact protrusions 24. The inner diameter, number, and interval of the contact protrusions 24 may be determined appropriately to meet design demands, when necessary. The contact protrusions 24, the first substrate 10, and/or the second substrate 20 may, suitably, be treated with plasma to exhibit a higher hydrophilic property so that they can be more strongly adhered with the viscous composition(s) 13, 23.

Also preferably, the step (a) may comprise the steps of: forming a first bottom layer 11 on the first substrate 10 by applying a first viscous material on the first substrate and solidifying the applied first viscous material; forming a first top layer 12 on the first bottom layer 11 by applying a second viscous material on the inner surface of the first bottom layer 11 and solidifying the applied second viscous material; and spotting the first viscous composition 13 on the first top layer 12.

The first bottom layer 11 and/or the first top layer 12 may be formed as a continuous layer or a discontinuous layer comprising a plurality of spots spaced apart from each other. In case where both the first bottom layer 11 and the first top layer 12 are discontinuous layers or where the first bottom layer 11 is a continuous layer and the first top layer 12 is a discontinuous layer, the first viscous composition 13 is spotted on all or part of the plurality of spots of the first top layer 12. The first viscous material may be the same as or different from the second viscous material.

Preferably, the step (c) may comprise elongating the viscous composition to a desired length (e.g., 10 to 5000 μm) at a speed (e.g., 0.8 to 2000 μm/s) while air is blown at a blowing speed (e.g., 1 to 100 m/s). Also preferably, the step (c) may comprise elongating the viscous composition to a desired length (e.g., 10 to 5000 μm) at a speed (e.g., 0.8 to 2000 μm/s) while air is not blown.

Also preferably, the step (c) may comprise the steps of: (c-1) elongating the first viscous composition 13 for a first predetermined time period; (c-2) stopping the elongation for a second predetermined time period; and (c-3) further elongating the elongated first viscous composition 13 for a third predetermined time period. The elongation speed and time, the time between the first elongation and the second elongation, and the time and speed of air blowing are not limited to particular values and can be controlled according to design demands with regard to the final microstructures.

As a non-limiting example, the step (c) may be performed by elongating the viscous composition 13 containing an active ingredient at a speed of 3 to 20 μm/s for 5 to 15 seconds with/without blowing, stopping the elongation with/without blowing for seconds or minutes to thereby strengthening the contact between the viscous composition 13 and the substrate, and further elongating it with/without blowing to a desired length at a speed of 5 to 50 μm/s for 5 to 60 seconds. More specifically, when the primary lifting step is performed at a speed of 3 to 20 μm/s for 5 to 15 seconds without air blowing, the viscous composition may be adhered to the second substrate, thereby forming an intermediate structure with a small diameter.

As another non-limiting example, the step (c) may be performed by primarily elongating the viscous composition to a desired length (e.g., 10 to 5000 μm) at a speed of 0.8 to 2000 μm/s while air is not blown, stopping the elongation for 1 to 100 seconds, and secondarily elongating the viscous composition to a desired length (e.g., 10 to 5000 μm) at a speed of 0.8 to 2000 μm/s while air is blown at a blowing speed of 1 to 100 m/s. As still another non-limiting example, the step (c) may be performed by primarily elongating the viscous composition to a desired length at a speed of 0.8 to 2000 μm/s while air is not blown, stopping the elongation for 1 to 100 seconds, and secondarily elongating the viscous composition to a desired length at a speed of 0.8 to 2000 μm/s. As a further non-limiting example, the step (c) may be performed by primarily elongating the viscous composition to a desired length (10 to 5000 μm) at a speed of 0.8 to 2000 μm/s while air is not blown, stopping the elongation for 1 to 100 seconds while blowing air at a blowing speed of 1 to 100 m/s, and secondarily elongating the viscous composition to a desired length (10 to 5000 μm) at a speed of 0.8 to 2000 μm/s while air is blown at a blowing speed of 1 to 100 m/s.

The step (d) may be performed by stopping the elongation or allowing the elongation to be made very slowly. The step (d) may be performed while air is blown or not blown. In case where air is blown, as described above, it may be blown directly or indirectly to the viscous composition. It also may be blown continuously or intermittently to the viscous composition. In some cases, it may be blown through at least one of the through holes 25. As shown in FIGS. 5D and 5E, for example, if air is blown through the through holes 25 in the step (d), since a blowing-exposed portion of the viscous composition 13 adhered to the contact protrusions 24 occupies a larger area, the blowing-exposed portion may condense faster than a portion of the viscous composition 13 below the adhered portion and form an intermediate structure and a portion of the viscous composition below the intermediate structure may be concentrated on the intermediate structure and condensed. A preferable blowing speed is 1 to 100 m/s, to which the present invention, however, is not limited.

The length of the intermediate structure is less than that of a final microstructure. Because the viscous composition 13 is condensed and solidified centering on the intermediate structure during the blowing of air to the viscous composition 13, the final microstructure has an effective length and a hardness to enable skin penetration.

In the step (e), the cutting may be performed using various methods, for example, a physical cutting process or a laser cutting process. In some cases, the step (e) may be performed by relatively rapidly moving the first substrate 10, the second substrate 20, or both. The resulting microstructure according to the present invention may be formed in various forms, including a microneedle, a microblade, a microknife, a microfiber, a microspike, a microprobe, a microbarb, a microarray, or a microelectrode.

Preferably, the microstructure has a shape that the diameter gradually decreases from the base thereof toward the top thereof. A preferable ratio of the diameter of the top to the base may range from 1:1.5 to 1:1000. Another preferable ratio may range from 1:3 to 1:5. A preferable diameter of the top portion of the microstructure may be 1 to 500 μm, 2 to 300 μm, or 5 to 100 μm. The diameter of the top is closely associated with the strength of a finally manufactured microstructure and proportional to the entire volume of the finally manufactured microstructure. A preferable effective length of the microstructure is 100 to 10,000 μm, 200 to 10,000 μm, 300 to 8,000 μm, or 500 to 2,000 μm. The term "effective length" used herein refers to a vertical length from the top of the microstructure to the surface of the substrate. The diameter, length, ratio, and/or shape of the microstructure, however, may be controlled by varying at least one of the conditions including the diameter of the contact protrusions, the wind speed, and the viscosity of the viscous composition, depending on the design demands, as described below.

Preferably, at least a portion of a microstructure manufactured by the methods according to certain embodiments of the present invention may contain an active ingredient that can induce a first pharmacological or cosmetic effect when being introduced into a subject and at least one of the other portions of the microstructure may contain a different active ingredient that can, when being introduced into a subject, induce a pharmacological or cosmetic effect that is the same as or different from the first pharmacological or cosmetic effect.

A method of manufacturing a microstructure according to a modified embodiment may comprise the steps of: (a) facing the inner surface of the first substrate with the inner surface of the second substrate, wherein the first substrate has the first viscous composition formed directly or indirectly on the inner surface of the first substrate; (b) moving the first substrate, the second substrate, or both at a first speed so as to allow the first viscous composition and the second substrate to become in contact with each other; (c) blowing air directly or indirectly to the first viscous composition to solidify the first viscous composition; and (d) moving the first substrate, the second substrate, or both at a second speed higher than the first speed so as to cut the solidified first viscous composition.

The methods according to the first embodiment and those according to the following second and third embodiments have components and steps, to some extent, in common, the detailed description of which will be omitted below.

Second Embodiment

Figure 10:
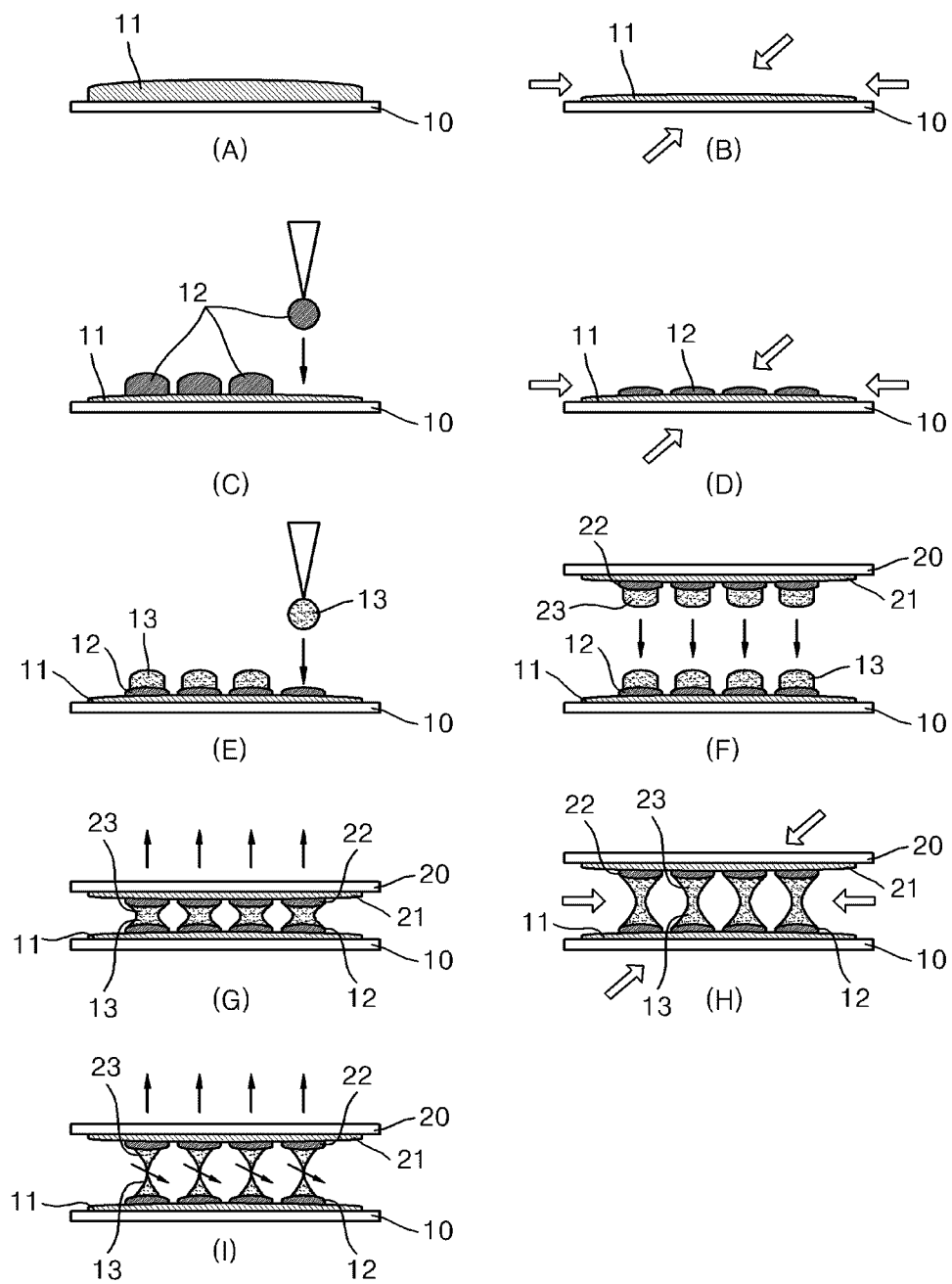
FIG. 10 is a diagram illustrating an example of the method for manufacturing a microstructure according to the second embodiment of the present invention.

Referring to FIG. 10, a method of manufacturing a microstructure according to the second embodiment comprises the steps of: (a) facing the inner surface of a first substrate 10 with the inner surface of a second substrate 20, wherein the first substrate 10 has a first viscous composition 13 spotted directly or indirectly on the inner surface of the first substrate 10 at predetermined positions and the second substrate 20 has a second viscous composition 23 spotted directly or indirectly on the inner surface of the second substrate 20 at predetermined positions; (b) moving the first substrate 10, the second substrate 20, or both so as to allow the first viscous composition 13 and the second viscous composition 23 to become in contact with each other; (c) moving the first substrate 10, the second substrate 20, or both so as to allow the first viscous composition 13 and the second viscous composition 23 to be elongated; (d) solidifying the elongated first and second viscous compositions 13, 23; and (e) cutting the solidified first and second viscous compositions 13, 23 at predetermined positions between the first substrate 10 and the second substrate 20 to provide a microstructure. As described above, at least one of the steps (a) to (e) may be performed while air is blown and air may be blown in many ways. The method, however, may be performed without air blowing.

Preferably, the step (a) may comprise the steps of: forming a first bottom layer 11 on the first substrate 10 by applying a first viscous material on the inner surface of the first substrate 10, solidifying the applied first viscous material, and spotting the first viscous composition 13 on the first bottom layer 11; and forming a second bottom layer 21 on the second substrate 20 by applying a second viscous material on the inner surface of the second substrate 20, solidifying the applied second viscous material, and spotting the second viscous composition 23 on the second bottom layer 21. The first viscous material may be the same as or different from the second viscous material. The first viscous composition 13 may be the same as or different from the second viscous composition 23.

The first bottom layer 11 may be formed as a continuous layer or a discontinuous layer comprising a plurality of spots spaced apart from each other. In case where the first bottom layer 11 is formed as a discontinuous layer, the first viscous composition may, suitably, be spotted on all or part of the plurality of spots of first bottom layer 11. Likewise, the second bottom layer 21 may be formed as a continuous layer or a discontinuous layer comprising a plurality of spots spaced apart from each other. In case where the second bottom layer 21 is formed as a discontinuous layer, the second viscous composition 23 may, suitably, be spotted on all or part of the plurality of spots of the second bottom layer 11.

Also preferably, the step (a) may comprise the steps of: forming a first bottom layer 11 on the first substrate 10 by applying a first viscous material on the inner surface of the first substrate 10, solidifying the applied first viscous material, forming a first top layer 12 on the first bottom layer 11 by applying a second viscous material on the first bottom layer 11, solidifying the applied second viscous material, and spotting the first viscous composition 13 on the first top layer 12; and forming a second bottom layer 21 on the second substrate 20 by applying a third viscous material on the inner surface of the second substrate 20, solidifying the applied third viscous material, forming a second top layer 22 on the second bottom layer 21 by applying a fourth viscous material on the second bottom layer 21, solidifying the applied fourth viscous material, and spotting the second viscous composition 23 on the second top layer 22. The first, second, third, and fourth viscous materials may be identical or different. The first viscous composition 13 may be the same as or different from the second viscous composition 23.

The first bottom layer 11 and/or the first top layer 12 may be formed as a continuous layer or a discontinuous layer comprising a plurality of spots spaced apart from each other. In case where both the first bottom layer 11 and the first top layer 12 are discontinuous layers or where the first bottom layer 11 is a continuous layer and the first top layer 12 is a discontinuous layer, the first viscous composition 13 is spotted on all or part of the plurality of spots of the first top layer 12. Likewise, the second bottom layer 21 and/or the second top layer 22 may be formed as a continuous layer or a discontinuous layer comprising a plurality of spots spaced apart from each other. In case where both the second bottom layer 21 and the second top layer 22 are discontinuous layers or where the second bottom layer 21 is a continuous layer and the second top layer 22 is a discontinuous layer, the second viscous composition 13 is spotted on all or part of the plurality of spots of the second top layer 22.

Preferably, the step (c) may comprise the steps of: (c-1) elongating the first and second viscous compositions 13, 23 for a first predetermined time period; (c-2) stopping the elongation for a second predetermined time period; and (c-3) further elongating the elongated first and second viscous compositions 13, 23 for a third predetermined time period.

Preferably, the first viscous composition 13 and/or the second viscous composition 23 may contain only a viscous material. Also preferably, the first viscous composition 13 may contain at least one first active ingredient that can induce a pharmacological or cosmetic effect when being introduced into a subject and the second viscous composition 23 may contain at least one second active ingredient that can induce a pharmacological or cosmetic effect when being introduced into a subject. The first active ingredient may be the same as or different from the second active ingredient. In case where the first and second active ingredients are different, the pharmacological or cosmetic effect induced by the first active ingredient may be the same as or different from the pharmacological or cosmetic effect induced by the second active ingredient . Preferably, the active ingredient(s) may be contained as a nano- or micro- particle or an emulsion form, as show in FIG. 9.

Preferably, the first viscous composition 13 and/or the second viscous composition 23 may contain at least one biocompatible material, at least one biodegradable material, or a combination thereof. Preferably, at least a portion of a microstructure manufactured by the methods according to certain embodiments of the present invention may contain an active ingredient that can induce a first pharmacological or cosmetic effect when being introduced into a subject and at least one of the other portions of the microstructure may contain a different active ingredient that can, when being introduced into a subject, induce a pharmacological or cosmetic effect that is the same as or different from the first pharmacological or cosmetic effect.

A method of manufacturing a microstructure according to a modified embodiment may comprise the steps of: (a) facing the inner surface of a first substrate with the inner surface of a second substrate, wherein the first substrate has a first viscous composition spotted directly or indirectly on the inner surface of the first substrate at predetermined positions and the second substrate has a second viscous composition spotted directly or indirectly on the inner surface of the second substrate at predetermined positions; (b) moving the first substrate, the second substrate, or both at a first speed so as to allow the first viscous composition and the second viscous composition to become in contact with each other; (c) blowing air directly or indirectly to the first and second viscous compositions to solidify the first and second viscous compositions; and (d) moving the first substrate, the second substrate, or both at a second speed higher than the first speed so as to cut the solidified first and second viscous compositions.

According to the embodiments, as a microstructure is obtained from the first substrate 10 and another microstructure is obtained from the second substrate 20 in the step (e), the overall productivity of the manufacturing process can be improved and loss of active ingredients can be eliminated or minimized.

Third Embodiment

Figure 12:
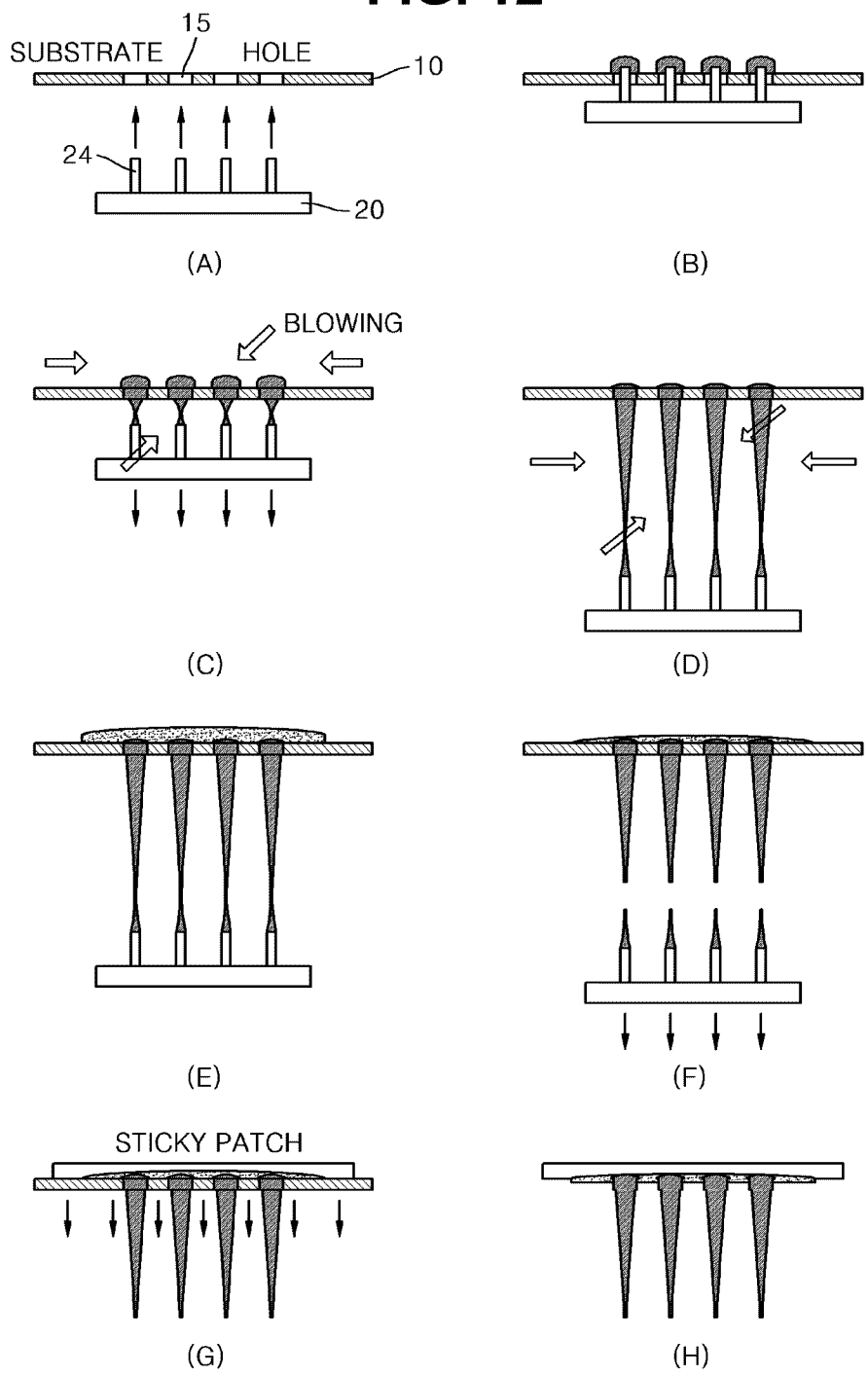
FIG. 12 is a diagram illustrating another example of the method for manufacturing a microstructure according to the third embodiment of the present invention.

Referring to FIGS. 11 to 13, a method of manufacturing a microstructure according to the third embodiment may comprise the steps of: (a) facing the inner surface of a first substrate 10 with the inner surface of a second substrate 20, wherein the first substrate 10 has a plurality of through holes 15 and the second substrate has a plurality of contact protrusions 24 each protruding by a predetermined length from the inner surface of the second substrate 20; (b) forming a first viscous composition 10 directly or indirectly on the outer surface of the first substrate 10; (c) moving the first substrate 10, the second substrate 20, or both so that the contact protrusions 24 are inserted into the through holes 15 thereby allowing the first viscous composition 13 and the contact protrusions 24 to become in contact with each other; (d) moving the first substrate 10, the second substrate 20, or both so as to allow the first viscous composition 13 to be elongated; (e) solidifying the elongated first viscous composition 13; and (f) cutting the solidified first viscous composition 13 at predetermined positions between the first substrate 10 and the second substrate 20 to provide a microstructure. As described above, at least one of the steps (a) to (f) may be performed while air is blown and air may be blown in many ways. The method, however, may be performed without air blowing.

The first viscous composition 10 may be formed on the outer surface of the first substrate 10 as a continuous layer or a discontinuous layer. In case where the first viscous composition 10 is formed as a discontinuous layer; the first viscous composition 10 may, suitably, be spotted to cover at least one of the through holes 15.

Preferably, the second substrate 20 may have a plurality of through holes 25. Preferably, the distance between the centers of any two of the through holes 25 may be set to be equal to the distance between the centers of any two of the contact protrusions 24. Preferably, the diameters of the through holes 15 are greater than the diameters of the contact protrusions 24. Air can be blown through at least one of the through holes 25 and/or at least one of the through holes 15 in at least one of the steps (a) to (f).

Preferably, a sticky patch may be attached on the outer surface of the first viscous composition 13. Alternatively, e.g., in case where the first viscous composition 13 is formed as a discontinuous layer, a continuous layer of a first viscous material is formed on the outer surface of the fist viscous composition 13 and the sticky patch is then attached on the outer surface of the continuous layer of the first viscous material. The first viscous material may be the same as or different from first viscous composition.

Preferably, the step (d) may comprise the steps of: elongating the first viscous composition 13 for a first predetermined time period; stopping the elongation for a second predetermined time period; and further elongating the elongated first viscous composition 13 for a third predetermined time period. The speed of elongation (i.e., the speed of movement of the substrate(s)) may be the same as or different from the speed of the further elongation. As a non-limiting example, the step (d) may comprise the steps of: (d-1) elongating the first viscous composition 13 by moving the second substrate 20 at a low speed (e.g., 0.2-0.4 mm/min), (d-2) further elongating the first viscous composition 13 by moving the second substrate 20 at a high speed (e.g., 5.0 to 7.0 mm/min); and (d-3) still further elongating the first viscous composition 13 by moving the second substrate 20 at a low speed (e.g., 0.1 to 0.15 mm/min) During or after at least one of the steps (d-1) to (d-3), the elongation of each of the steps can be stopped for seconds or minutes. Also during or after at least one of the steps (d-1) to (d-3), air can be blown. As described above, this can contribute to tightly combining e the contact protrusions 24 with the viscous composition 13. The step (d-2) may contribute to reduce or minimize the diameter of a middle portion of an intermediate structure to be finally prepared, so that the middle portion of the intermediate structure can be cut during separation of the microstructures from contact protrusions 24. A cut portion may correspond to a top of a finally manufactured microstructure. With the step (d-3), the base of a finally manufactured microstructure can have a sufficient diameter (e.g., 300 μm) and a sufficient strength.

Preferably, the first viscous composition 13 may contain only a viscous material. Also preferably, the first viscous composition 13 may contain at least one active ingredient that can induce a pharmacological or cosmetic effect if it is when being introduced into a subject. Preferably, the active ingredient(s) may be contained as a nano- or micro- particle or an emulsion form. Preferably, the first viscous composition 13 may contain at least one biocompatible material, at least one biodegradable material, or a combination thereof. Preferably, at least a portion of the microstructure manufactured by the methods of the first embodiment of the present invention may contain an active ingredient that can induce a first pharmacological or cosmetic effect when being introduced into a subject and at least one of the other portions of the microstructure may contain a different active ingredient that can, when being introduced into a subject, induce a pharmacological or cosmetic effect that is the same as or different from the first pharmacological or cosmetic effect.

A method of manufacturing a microstructure according to a modified embodiment may comprise the steps of: (a) facing the inner surface of a first substrate with the inner surface of a second substrate, wherein the first substrate has a plurality of through holes and the second substrate has a plurality of contact protrusions each protruding by a predetermined length from the inner surface of the second substrate; (b) forming a first viscous composition directly or indirectly on the outer surface of the first substrate; (c) moving the first substrate, the second substrate, or both at a first speed so that the contact protrusions are inserted into the through holes thereby allowing the first viscous composition and the contact protrusions to become in contact with each other; (d) moving the first substrate, the second substrate, or both so as to allow the first viscous composition to be elongated to a predetermined length; (e) blowing air directly or indirectly to the first viscous composition to solidify the first viscous composition; and (f) moving the first substrate, the second substrate, or both at a second speed higher than the first speed so as to cut the solidified first viscous composition.

Figure 17:
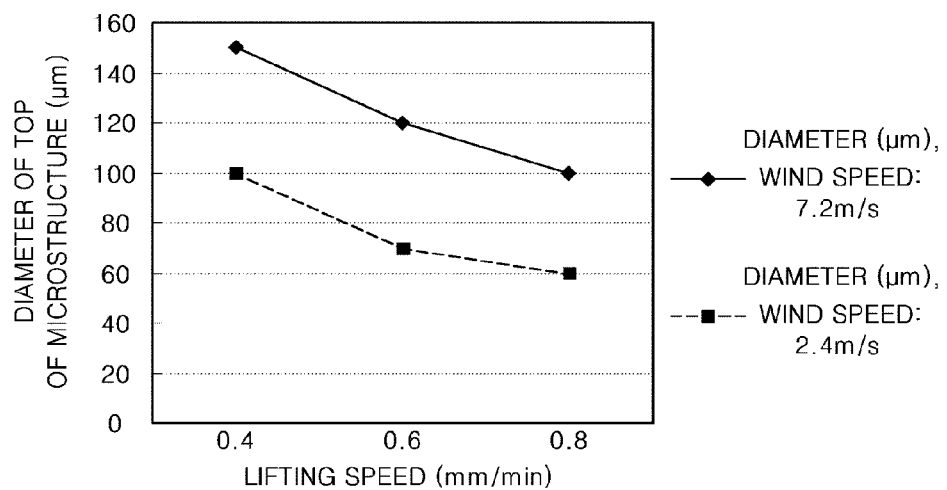
FIGS. 17 to 19 are graphs showing the effect of the speed of air blown and the speed of the movement of a substrate on the top diameter of a microstructure.
Figure 18:
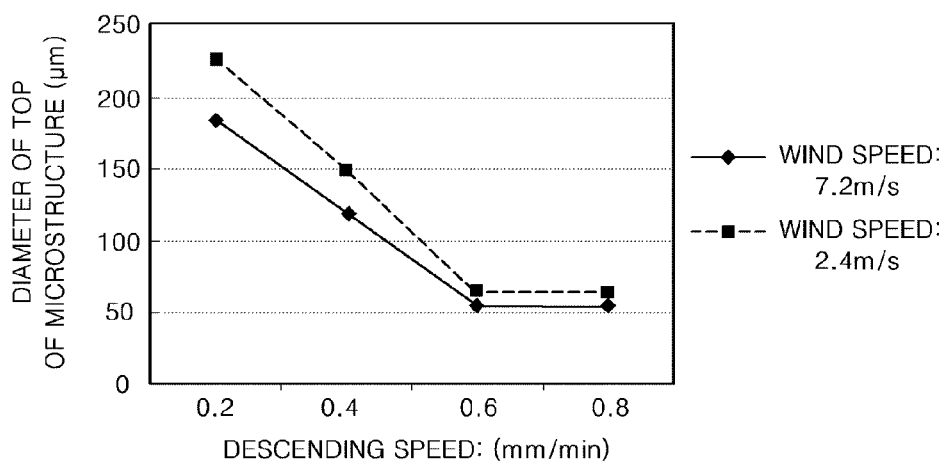
Figure 19:
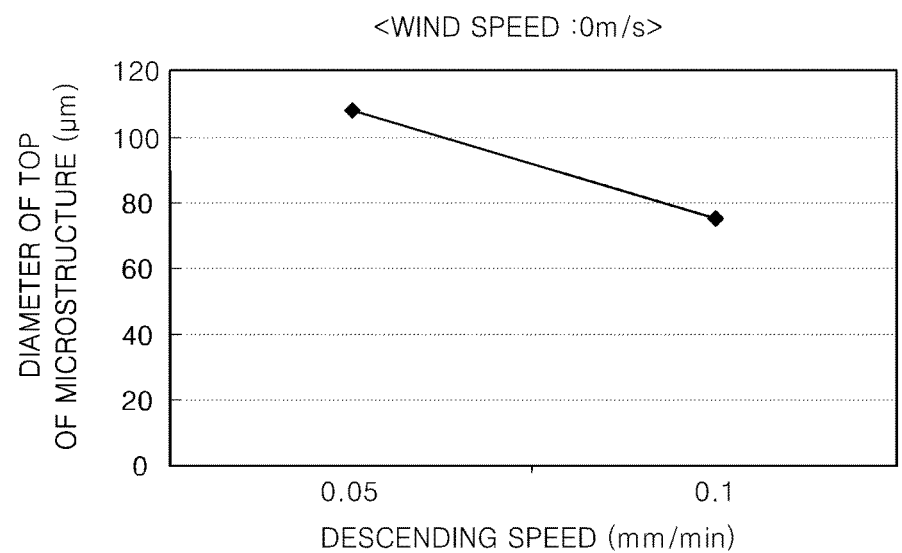

According to the above-described first to third embodiments and modified embodiments thereof, the shape (e.g., diameters of the top and bases of the microstructures, distance between the tops and bases, and diameter of a middle portion between the tops and bases) and hardness of the final microstructures were able to be changed by appropriately controlling factors including the moving speed of the first and/or second substrate 10, 20, the inner diameter of the contact protrusions 24, the air blowing speed, and the viscosity of the viscous materials (cf. FIGS. 16-19). In general, the diameter of the top of the microstructure may be reduced with a rise in the moving speed of the substrate(s), a reduction in the inner diameter of the contact protrusions 24, a reduction in the air blowing speed, and a reduction in the viscosity of the viscous material(s). The experimental data shown in FIGS. 17-19 show the effect of air blowing speed and substrate movement speed on the diameter of the top of the microstructure.

Figure 20:
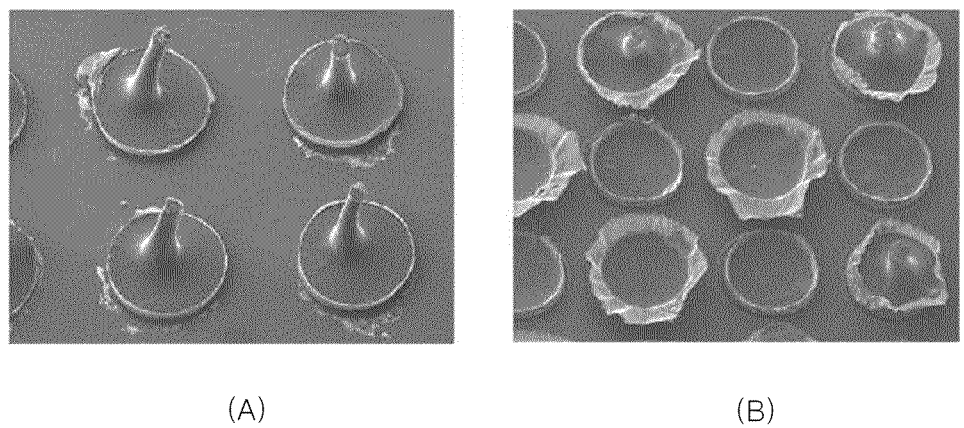
FIG. 20A is a photograph of a microstructure manufactured with air blowing and FIG. 20B is a photograph of a microstructure manufactured without air blowing.
Figure 21:
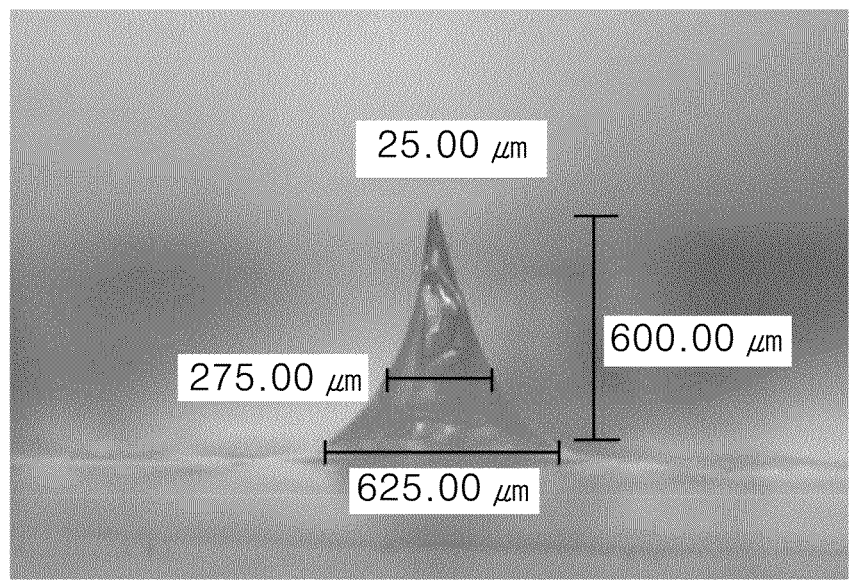
FIG. 21 is a photograph showing morphologic features of a microstructure manufactured by a method of the present invention.
Figure 22:
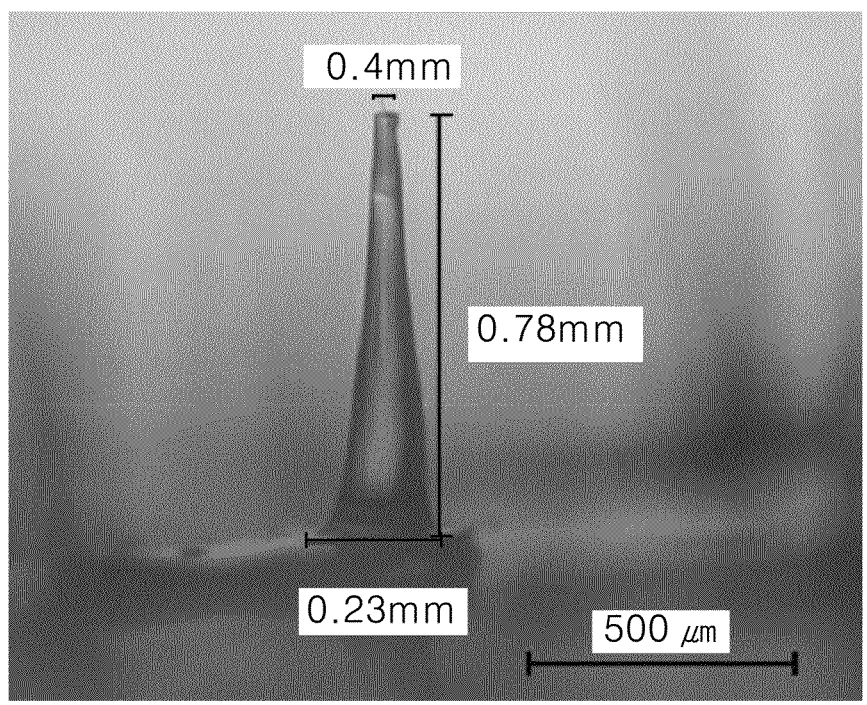
FIG. 22 is a photograph showing morphologic features of a microstructure manufactured by another method of the present invention.

FIG. 20A is a photograph of a microstructure manufactured with air blowing according to the third embodiment and FIG. 20B is a photograph of a microstructure manufactured without air blowing, which show that air blowing can be a factor in determining the shape of the microstructure. In FIGS. 20A and 20B, the circular bottom structures are formed due to the through holes of the substrate(s) and the size there of is the same or substantially the same as that of the through holes. In FIG. 20B, a thin layer is formed around each of the circular structures. Without intending to limit the theory, the thin layer is believed to be formed by solidifying a portion of the viscous composition 13 passing through an outermost portion of each of the through holes. By comparison, in FIG. 20A, because of air blowing, the viscous composition 13 is not allowed to pass through the through holes. FIGS. 21 and 22 are photographs of microstructures manufactured by a method of the present invention.

EXAMPLES

The present invention will now be described more fully with reference to the accompanying drawings, in which exemplary embodiments of the invention are shown. The exemplary embodiments should be considered in a descriptive sense only and not for purposes of limitation. Therefore, it will be apparent to those skilled in the art that the scope of the invention is not limited by the exemplary embodiments.

Example I

Carboxymethylcellulose (CMC)

Figure 14:
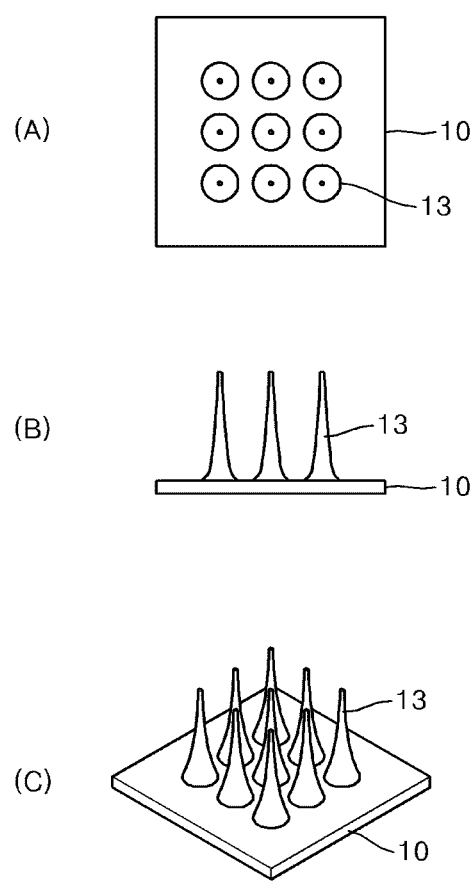
FIGS. 14A to 14C illustrate an example of a microstructure manufactured by the methods for manufacturing a microstructure according to the first, second, and third embodiments of the present invention.
Figure 15:
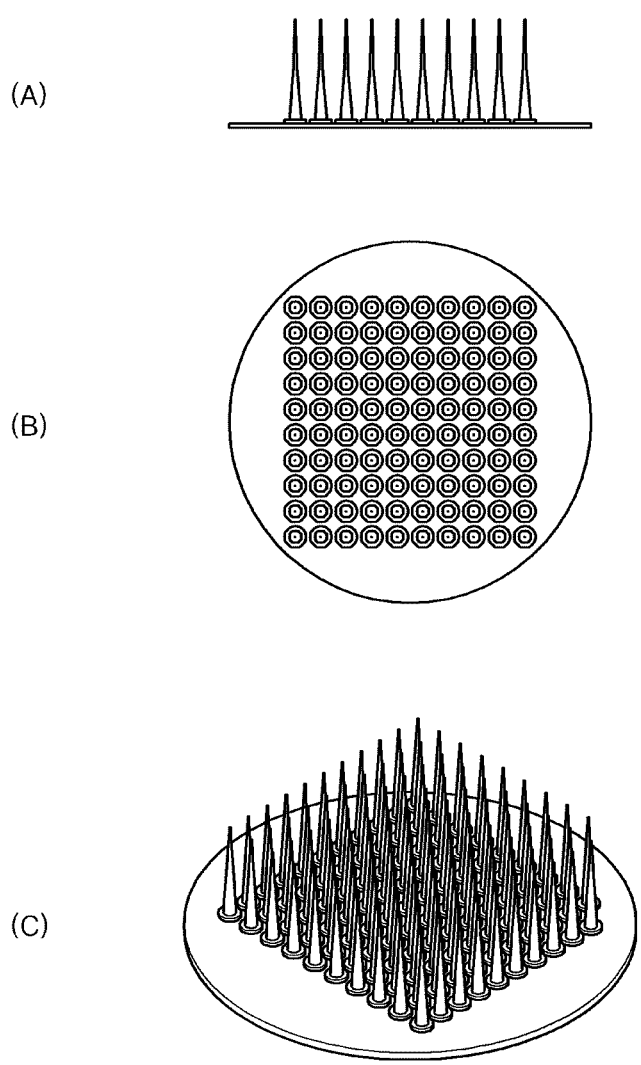
FIGS. 15A to 15C illustrate another example of a microstructure manufactured by the methods for manufacturing a microstructure according to the first, second, and third embodiments of the present invention.

0.4 mg of a high-viscosity CMC (Sigma) was dissolved in 20 ml of tertiary distilled water to obtain a 2% (w/v) CMC solution as viscous composition (13). The CMC viscous composition was coated on a first substrate (glass) substrate 10 (FIG. 5A). A second substrate 20 having thereon 3×3 contact protrusions 24, each of which has a diameter of 500 μm, was contacted with the first substrate 10 (FIG. 5B). Thereafter, air was weakly blown (not shown) for 5 minutes through the through holes 25 of the second substrate 20, thereby weakly solidifying the CMC viscous composition so as to be strongly contacted with the contact protrusions 24 (FIG. 5B). The second substrate 20 was lifted at a speed of 11.945 μm/s for 1 minute to the entire lifting height of 716.7 μm, thereby forming an intermediate structure (FIG. 5C). Moisture was removed from the CMC viscous composition while continuously blowing air through the through holes 25 of the second substrate 20 (FIG. 5D). By removing moisture, the CMC viscous composition was solidified over an area between the second substrate 20 and the first substrate 10 (FIG. 5E). The solidified area was cut by microscissors to produce microneedles (FIG. 5F). As a result, 3×3 microneedles (FIG. 14) each having a top diameter of 50 μm and an effective length of 1,200 μm were manufactured.

The diameter of the microneedles was able to be controlled by varying the diameter of the contact protrusions 24. Also, the shape of the microneedles was able to be changed by varying the speed of the air blowing through the through holes 25 or the viscosity of CMC.

For instance, when a 10% (w/v) solution prepared by a low-viscosity CMC (Sigma) was used, microneedles having a greater diameter were manufactured.

Chitosan 10 ml of tertiary distilled water is mixed with 100 μl of acetic acid and 0.46 g of a low-molecular-weight chitosan (Sigma) is dissolved in the resulting mixture to prepare a 30% (w/v) chitosan solution as a viscous composition. 100 μl of the chitosan viscous composition was coated on a first substrate 10 (FIG. 5A). A second substrate 20 having 4×4 contact protrusions, each of which has a diameter of 400 μm, was contacted with the chitosan viscous composition. Thereafter, air was weakly blown (not shown) for 5 minutes through the through holes 25 of the second substrate 20, thereby weakly solidifying the chitosan viscous composition so as to be strongly contacted with the contact protrusions 24 (FIG. 5B). While maintaining the weak air blowing, the second substrate 20 was lifted at a speed of 0.6 mm/min for 30 seconds and then slowly lifted at a speed of 0.2 mm/min for 2 minutes and 30 seconds, thereby forming an intermediate structure (FIG. 5C). Moisture was removed from the CMC viscous composition while blowing air through the through holes 25 of the second substrate 20 (FIG. 5D). Then, the chitosan viscous composition was solidified, while strongly blowing air for 15 to 20 minutes, over an area between the second substrate 20 and the first substrate 10 (FIG. 5E). The solidified area was cut by microscissors to produce microneedles (FIG. 5F).

As a result, 4×4 microneedles (not shown) each having a top diameter of 50 μm and an effective length of 800 μm were manufactured. As described above, the diameter and length of microneedles were able to be controlled by varying the diameter of the contact protrusions and the lifting speed and time.

Hyaluronic Acid Sodium Salt 0.2 g of hyaluronic acid having a low molecular weight of 10,000 to 15,000 and 0.3 g of hyaluronic acid having a high molecular weight of 1,000,000 to 1,500,000 were dissolved in 10 ml of tertiary distilled water, thereby producing a 33% (w/v) hyaluronic acid viscous composition. 100 μl of the hyaluronic-acid viscous composition was coated on a first substrate 10. A second substrate 20 having 4×4 contact protrusions, each of which has a diameter of 400 μm, was contacted with the hyaluronic acid viscous composition. Thereafter, air was weakly blown (not shown) for 5 minutes, thereby weakly solidifying the hyaluronic acid viscous composition so as to be strongly contacted with the contact protrusions 24 (FIG. 5B). While maintaining the weak air blowing, the second substrate 20 was lifted at a speed of 0.6 mm/min for 30 seconds and then slowly lifted at a speed of 0.2 mm/min for 2 minutes and 30 seconds, thereby forming an intermediate structure (FIGS. 5B through 5D). Then the hyaluronic acid viscous composition was solidified, while strongly blowing air for 15 to 20 minutes, over an area between the second substrate 20 and the first substrate 10 (FIG. 5E). The solidified area was cut by microscissors to produce microneedles (FIG. 5F).

As a result, 4×4 microneedles (not shown) each having a top diameter of 40 μm and an effective length of 800 μm were manufactured. As described above, the diameter and length of the microneedles were able to be controlled by varying the diameter of the contact protrusions and the lifting speed and time.

Hyaluronic Acid Sodium Salt & CMC 0.2 g of CMC and 0.2 g of hyaluronic acid having a high molecular weight of 1,000,000 to 1,500,000 were dissolved in 20 ml of tertiary distilled water, thereby producing a viscous composition. The viscous composition was coated on a first substrate 10 (FIG. 5A). A second substrate 20 having 4×4 contact protrusions, each of which has a diameter of 500 μm, was contacted with the viscous composition. Thereafter, air was weakly blown (not shown) through the through holes for 5 minutes, thereby weakly solidifying the viscous composition so as to be strongly contacted with the contact protrusions 24 (FIG. 5B). The second substrate 20 was lifted for 1 minute at a speed of 0.6 mm/min and then slowly lifted for 3 minutes at a speed of 0.1 mm/min. In this case, the second substrate 20 was lifted to a total height of 900 μm, thereby forming an intermediate structure (FIG. 5C). Moisture was removed from the viscous composition while continuously blowing air through the through holes 25 of the substrate 20 (FIG. 5D). By removing moisture, the viscous composition was solidified over an area between the second substrate 20 and the first substrate 10 (FIG. 5E). The solidified area was cut by microscissors to produce microneedles (FIG. 5F).

As a result, 4×4 microneedles (not shown) each having a top diameter of 50 μm and an effective length of 1,200 μm were manufactured. As described above, the diameter and length of the microneedles were able to be controlled by varying the diameter of the contact protrusions and the lifting speed and time.

Example II

To observe a variation in the diameter of microstructures relative to the diameter of contact protrusions, microstructures having different diameters (i.e., 200 μm, 250 μm, 300 μm, 350 μm, 400 μm, 450 μm, and 500 μm) were manufactured. 0.3 g of a low-viscosity CMC (Sigma) was dissolved in 30 ml tertiary distilled water to produce a CMC viscous composition. The CMC viscous composition was coated on a first substrate 10 (FIG. 5A). A second substrate 20 having 4×4 contact protrusions, each of which has a diameter of 200 to 500 μm, was contacted with the viscous composition Thereafter, air was weakly blown (not shown) through the through holes for 5 minutes, thereby weakly solidifying the viscous composition so as to be strongly contacted with the contact protrusions 24 (FIG. 5B). The second substrate 20 was lifted for 1 minute at a speed of 0.6 mm/min and then slowly lifted for 3 minutes at a speed of 0.1 mm/min. In this case, the second substrate 20 was lifted to a total height of 900 μm, thereby forming an intermediate structure (FIG. 5C). Moisture was removed from the viscous composition while continuously blowing air through the through holes 25 of the substrate 20 (FIG. 5D). By removing moisture, the viscous composition was solidified over an area between the second substrate 20 and the first substrate 10 (FIG. 5E). The solidified area was cut by microscissors to produce microneedles (FIG. 5F).

As a result, it was identified that when the contact protrusions had a diameter of 300 μm or more, the size of the contact protrusions was proportional to the diameter of the microneedles.

Example III

CMC 3 mg of a low-viscosity CMC was dissolved in 30 ml tertiary distilled water to prepare to produce a 10% CMC viscous composition. The viscous composition was coated on a first substrate 10 and air was blown (FIGS. 4A and 4B). Subsequently, the viscous composition was spotted, e.g., by using a dispenser nozzle 26 and air was blown (FIGS. 4C and 4D). A viscous composition containing a drug was spotted (FIG. 4E),. A second substrate 20 having 3×3 contact protrusions, each of which has a diameter of 500 μm, was descended and contacted with the viscous composition containing a drug (FIG. 4F). The second substrate 20 was then primarily lifted for 5 to 15 seconds at a speed of 10 μm/s. After 5 minutes elapsed, air was blown while secondarily lifting the second substrate 20 for 10 to 60 seconds at a speed of 5 to 50 μm/s. The second substrate 20 was lifted to a total lifting height of 766.7 μm, thereby forming an intermediate structure 30 (FIG. 4G). It was confirmed that the shape of the resulting microneedles was able to be changed by adjusting the lifting speed and time. For example, when the second substrate 20 was lifted at a speed higher than a certain value (e.g., 50 μm/s) for 10 seconds or more, the intermediate structure could not be formed, and the attachment between CMC and the contact protrusions could be broken. Moisture was removed from the viscous composition by blowing air after the secondary lifting step (FIG. 4G). By removing moisture, the viscous composition containing a drug was solidified over an area between the first substrate 10 and the second substrate 20. The solidified area was cut by lifting the second substrate at a high speed.

As a result, microneedles each having a top diameter of 10 to 80 μm and an effective length of 500 to 3,000 μm were manufactured (FIG. 4H). In this case, as described above, the diameter of the microneedles was able to be controlled by varying the diameter of the contact protrusions. Also, the shape of the microneedles was able to be changed by varying the concentration (viscosity) of CMC. That is, as the concentration (viscosity) of CMC is higher, the amount of CMC contained in the same amount of viscous solution is higher, resulting in the increase in the diameter of the microneedles.

Chitosan

Microneedles were manufactured in the same method as described above except that a low-molecular-weight chitosan (Sigma) was used instead of CMC. More specifically, 0.92 g of chitosan was dissolved in 20 ml tertiary distilled water (1% $CH_3COOH$) to produce a viscous composition solution. Since chitosan has a lower viscosity than CMC, strong air blowing was performed for 3 minutes at the steps corresponding to FIGS. 4F and 4G after the viscous composition was loaded to make sure that a predetermined amount of moisture could be evaporated by the air to thereby increase the viscosity of the viscous composition. As a result, microneedles each having a top diameter of 50 μm and an effective length of 800 μm were manufactured.

Example IV 2.7 g of a low-molecular-weight CMC (Sigma) was dissolved in 30 ml tertiary distilled water to prepare a 9% (w/v) viscous composition solution. A second substrate 20 having 10×10 contact protrusions in a density of $100/1.5$ $cm^2$. Each of the contact protrusions has a diameter of 500 μm and the distance between the centers of adjacent contact protrusions was 1.6 mm. A stainless-steel solid substrate having a thickness of 0.1 mm and having through holes therein was used as a first substrate 10. Each of the through holes has a diameter of 900 μm and the distance between the centers of adjacent through holes of the first substrate was 1.6 mm. The second substrate 20 was lifted such that the centers of the contact protrusions of the second substrate 20 were matched with the centers of the through holes of the first substrate 10 and the upper ends of the contact protrusions were located about 0.2 mm above the through holes of the first substrate 10 (FIG. 12A). Afterwards, a CMC viscous composition solution containing a drug was spotted toward the respective holes of the first substrate (FIG. 12B). The second substrate 20 was then descended for 1 minute at a speed of 0.4 mm/min such that the viscous composition adhered to the contact protrusions was descended below the first substrate. The viscous composition was solidified by strongly blowing air for 5 minutes so as to be strongly adhered with the contact protrusions. Subsequently, the second substrate was rapidly descended for 10 seconds at a speed of 7.0 mm/min while air was blown at a high speed, the descending process was stopped, and air was blown at a high speed for 2 minutes. Finally, the second substrate was descended at a speed of 0.15 mm/min for 4 minutes by strongly blowing air (FIGS. 12C and 12D). By removing moisture, the viscous composition was solidified over an area between the first and second substrates. A small amount of a CMC viscous composition containing no drug was coated to cover all the holes of the first substrate (FIG. 12E). As a result, bases of the respective microstructures were strongly connected with one another and tightly fixed onto the substrate. After the CMC viscous composition was completely solidified by strong air blowing, the second substrate was descended by applying instantaneous force, causing middle portions of the microstructures with a small diameter to be cut (FIG. 12F). Finally, adhesive (sticky) patches were adhered to bases of the manufactured microneedles, and the microneedles were separated from the first substrate (FIGS. 12G and 12H).

As a result, microneedles with a top diameter of 50 μm and an effective length of 800 μm were manufactured. The top diameter, base diameter, effective length, and general shape of the microstructures were able to be controlled by varying the diameter of the contact protrusions, the viscosity of the viscous material, the air blowing speed, and the descending speed. It was confirmed that the diameter of the microstructures was reduced with a reduction in the diameter of the contact protrusions, a reduction in the viscosity of the viscous material, a reduction in the air blowing speed, and a rise in the descending speed.

Example V

Microneedles each having a small effective length of 300 μm, which may be applied for delivery of cosmetics, were manufactured. 2.7 g of a low-molecular-weight CMC (Sigma) CMC was dissolved in 30 ml tertiary distilled water to prepare a 9% (w/v) viscous composition solution. A second substrate 20 having 10×10 contact protrusions in a density of $100/6.6$ $mm^2$. Each of the contact protrusions has a diameter of 300 μm and the distance between the centers of adjacent contact protrusions was 700 μm. A stainless-steel solid substrate having a thickness of 100 μm and having through holes therein was used as a first substrate 10. Each of the through holes has a diameter of 500 μm and the distance between the centers of adjacent through holes of the first substrate was 700 μm. The second substrate 20 was lifted such that the centers of the contact protrusions of the second substrate 20 were matched with the centers of the through holes of the first substrate 10 and the upper ends of the contact protrusions were located about 0.2 mm above the through holes of the first substrate 10 (FIG. 11A).

Afterwards, a CMC viscous composition solution containing a drug was thinly coated on the first substrate (FIG. 11B). The second substrate 20 was descended for 1 minute at a speed of 0.4 mm/min such that the viscous composition adhered to the contact protrusions was descended below the first substrate. The viscous composition was solidified by strongly blowing air for 5 minutes so as to be strongly adhered with the contact protrusions. Subsequently, the second substrate was rapidly descended for 10 seconds at a speed of 7.0 mm/min while air was blown at a high speed, the descending process was stopped, and air was blown at a high speed for 2 minutes. Finally, the second substrate was descended at a speed of 0.1 mm/min for 2 minutes by strongly blowing air (FIGS. 11C and 11D).

By removing moisture, the viscous composition was solidified over an area between the first and second substrates. After the viscous composition was completely solidified by strong air blowing, the second substrate was descended by applying instantaneous force, causing middle portions of the microstructures with a small diameter to be cut (FIG. 11E). Finally, adhesive (sticky) patches were adhered to bases of the manufactured microneedles, and the microneedles were separated from the first substrate (FIGS. 11G and 11H).

As a result, microneedles each having a top diameter of 10 μm and an effective length of 300 μm were manufactured.

Example VI

Microneedles containing microparticles were manufactured. A water-soluble vitamin C derivative (ascorbic acid:

Sigma) was mixed with water serving as a solvent. A fat-soluble vitamin A derivative (retinol: Sigma) dissolved in dichloromethane (Sigma) serving as an organic solvent. They were emulsified in an O/W form using a homogenizer at a stirring speed of 11,000 rpm.

3 g of CMC was dissolved in 30 ml tertiary distilled water in which a vitamin C derivative and a vitamin A derivative were emulsified, thereby producing a 9% (w/v) viscous composition solution.

Microparticles of biodegradable PLA (Sigma) were produced using a multiple emulsion method to contain a calcein reagent (Sigma) and filtered using a filter (Millex) to leave only microparticles with a diameter of 5 mm or less. The prepared microparticles were mixed with CMC, thereby preparing, as a base material, emulsified CMC containing microparticles in which the calcein reagent was contained (FIG. 9B). A second substrate 20 having 10×10 contact protrusions in a density of 100/6.6 mm$^2$ Each of the contact protrusions has a diameter of 300 μm and the distance between the centers of adjacent contact protrusions was 700 m. A stainless-steel solid substrate having a thickness of 100 μm and having through holes therein was used as a first substrate 10. Each of the through holes has a diameter of 500 μm and the distance between the centers of adjacent through holes of the first substrate was 700 μm. The second substrate 20 was lifted such that the centers of the contact protrusions of the second substrate 20 were matched with the centers of the through holes of the first substrate 10 and the upper ends of the contact protrusions were located about 0.2 mm above the through holes of the first substrate 10 (see FIG. 11A).

The CMC base material containing microparticles was then uniformly coated on the substrate to a small thickness (see FIG. 11B). The second substrate 20 was descended for 1 minute at a speed of 0.4 mm/min such that the viscous composition adhered to the contact protrusions was descended below the first substrate. The viscous composition was solidified by strongly blowing air for 5 minutes so as to be strongly adhered with the contact protrusions. Subsequently, the second substrate was rapidly descended for 10 seconds at a speed of 7.0 mm/min while air was blown at a high speed, the descending process was stopped, and air was blown at a high speed for 2 minutes. Finally, the second substrate was descended at a speed of 0.1 mm/min for 2 minutes by strongly blowing air (see FIGS. 11C and 11D).

By removing moisture, the viscous composition was solidified over an area between the first and second substrates. After the viscous composition was completely solidified by strong air blowing, the second substrate was descended by applying instantaneous force, causing middle portions of the microstructures with a small diameter to be cut (FIG. 11E). Finally, adhesive (sticky) patches were adhered to bases of the manufactured microneedles, and the microneedles were separated from the first substrate (FIGS. 11G and 11H).

As a result, microneedles each having a top diameter of 10 μm and an effective length of 300 pm were manufactured (FIG. 9A). The concentration of the CMC base material were able to be changed according to the emulsified extent and the content of microparticles. The concentration of the CMC base material was disproportional to the content of the fat-soluble drug and the content of microparticles.

Example VII

Microstructures containing microparticles were manufactured. A water-soluble vitamin C derivative (ascorbic acid: Sigma) was mixed with water serving as a solvent. A fat-soluble vitamin A derivative (retinol: Sigma) dissolved in dichloromethane (Sigma) serving as an organic solvent. They were emulsified in an O/W form using a homogenizer at a stirring speed of 11,000 rpm.

3.5 mg of CMC was dissolved in 30 ml tertiary distilled water in which a vitamin C derivative and a vitamin A derivative were emulsified, thereby producing a 10% (w/v) viscous composition solution. Microparticles of biodegradable PLA (Sigma) were produced using a multiple emulsion method to contain a calcein reagent (Sigma) and filtered using a filter (Millex) to leave only microparticles with a diameter of 5 mm or less. The prepared microparticles were mixed with CMC, thereby preparing, as a base material, CMC mixed with a cy 5.5 reagent and containing microparticles in which the calcein reagent was contained (FIG. 9B).

After the 10% CMC composition was loaded on the substrate 10, the CMC base material containing microparticles was subsequently coated on the substrate while blowing air. Thereafter, after the CMC base material containing microparticles was dispensed and air was blown (FIGS. 4C and 4D). Then, a drug-containing viscous composition was dispensed on the structure (FIG. 4E), and a second substrate 20 having 3×3 contact protrusions, each of which has a diameter of 500 μm, was contacted with the first substrate 10 (refer to FIG. 4F). The second substrate 20 was lifted at a speed of 5 to 50 μm for 10 to 60 seconds to a total lifting height of 716.7 μm, thereby producing an intermediate structure (FIG. 4G). It was confirmed that the shape of microneedles was able to be changed by varying the lifting speed and time. When the second substrate 20 was lifted at a high lifting speed of 50 μm/s or more for 10 seconds or more, an attachment between CMC and the contact protrusions could be broken without forming the intermediate structure. Accordingly, the lifting speed should be controlled according to the kinds and concentrations (viscosity) of materials. After the second substrate 20 was lifted, moisture was removed from the CMC composition while blowing air (FIG. 4G). By removing moisture, the CMC composition was solidified over an area between the first and second substrates (FIG. 4H). The solidified area was cut by lifting the second substrate 20 at a high speed.

As a result, the resulting microneedles, each of which has a top diameter of 10 to 80 μm and an effective length of 500 to 3,000 μm, contain water-soluble and fat-soluble drugs and microparticles (FIG. 9A). In this case, the diameter of the microneedles were able to be controlled by varying the diameter of the contact protrusions. Also, it was confirmed that the shape of the solid microneedles was able to be changed by varying the concentration (viscosity) of CMC. That is, as the concentration (viscosity) of CMC is higher, the amount of CMC contained in the same amount of viscous composition is higher, resulting in the increase in the diameter of the microneedles. The concentration of the CMC base material was able to be changed according to the emulsified extent and the content of microparticles. That is, the concentration of the CMC base material was disproportional to the content of the fat-soluble drug and the content of the microparticles.

As explained in the above Examples, solid microstructures having desired properties (e.g., effective length, top diameter, and hardness) can be manufactured by controlling, the diameter of the microstructures should be controlled at least one of the factors including the lifting speed of the substrate(s), the diameter of the contact protrusions, the viscosity of the viscous composition, and the air blowing speed (FIG. 16). It should be noted that although the Examples describe methods of manufacturing microneedles, they may also be applied to the other various forms of microstructures, including microblades, microknives, microfibers, microspikes, microprobes, microbarbs, microarrays, and microelectrodes.

With the methods according to the embodiments and Examples, active ingredient(s) can be loaded with no or less loss, microstructures with desired properties can be manufactured in a simpler and more cost-effective way, processes (e.g., heat treatment) that may affect activities of active ingredients can be avoided, amount of active ingredient(s) that can be loaded on a unit area of a substrate can be increased; microneedles can be reused (e.g., cleaning microneedles and replacing patches); mutidrug delivery and controlled-release delivery can be provided.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

The invention claimed is:

1. A method of manufacturing a microstructure, the method comprising the steps of:
   (a) facing the inner surface of a first substrate with the inner surface of a second substrate, wherein the first substrate has a first viscous composition spotted directly or indirectly on the inner surface of the first substrate at predetermined positions and the second substrate has a second viscous composition spotted directly or indirectly on the inner surface of the second substrate at predetermined positions;
   (b) moving the first substrate, the second substrate, or both so as to allow the first viscous composition and the second viscous composition to become in contact with each other;
   (c) moving the first substrate, the second substrate, or both so as to allow the first viscous composition and the second viscous composition to be elongated;
   (d) solidifying the elongated first and second viscous compositions; and
   (e) cutting the solidified first and second viscous compositions at predetermined positions between the first substrate and the second substrate to provide a microstructure.

2. The method of claim 1, wherein at least one of the steps (a) to (e) is performed while air is blown.

3. The method of claim 1, wherein the step (a) comprises the steps of:
   (a-1) forming a first bottom layer on the first substrate by applying a first viscous material on the inner surface of the first substrate, solidifying the applied first viscous material, and spotting the first viscous composition on the first bottom layer; and
   (a-2) forming a second bottom layer on the second substrate by applying a second viscous material on the inner surface of the second substrate, solidifying the applied second viscous material, and spotting the second viscous composition on the second bottom layer.

4. The method of claim 3, wherein air is blown in at least one of the steps (a-1) and (a-2).

5. The method of claim 3, wherein the first bottom layer formed on the first substrate is a discontinuous layer comprising a plurality of spots spaced apart from each other, and the first viscous composition is spotted on all or part of the plurality of spots, and
   wherein the second bottom layer formed on the second substrate is a discontinuous layer comprising a plurality of spots spaced apart from each other, and the second viscous composition is spotted on all or part of the plurality of spots.

6. The method of claim 3, wherein the first viscous material is different from the second viscous material and the first viscous composition is different from the second viscous composition.

7. The method of claim 1, wherein the step (a) comprises the steps of:
   (a-1) forming a first bottom layer on the first substrate by applying a first viscous material on the inner surface of the first substrate, solidifying the applied first viscous material, forming a first top layer on the first bottom layer by applying a second viscous material on the first bottom layer, solidifying the applied second viscous material, and spotting the first viscous composition on the first top layer; and
   (a-2) forming a second bottom layer on the second substrate by applying a third viscous material on the inner surface of the second substrate, solidifying the applied third viscous material, forming a second top layer on the second bottom layer by applying a fourth viscous material on the second bottom layer, solidifying the applied fourth viscous material, and spotting the second viscous composition on the second top layer.

8. The method of claim 7, wherein air is blown in at least one of the steps (a-1) and (a-2).

9. The method of claim 7, wherein the first bottom layer formed on the first substrate, the first top layer formed on the first bottom layer, or both are discontinuous layers each comprising a plurality of spots spaced apart from each other, and the first viscous composition is spotted on all or part of the plurality of spots, and
   wherein the second bottom layer formed on the second substrate, the second top layer formed on the second bottom layer, or both are discontinuous layers each comprising a plurality of spots spaced apart from each other, and the second viscous composition is spotted on all or part of the plurality of spots.

10. The method of claim 7, wherein at lest one of the first, second, third, and fourth viscous materials is different from the other or others and the first viscous composition is different from the second viscous composition.

11. The method of claim 1, wherein the step (c) comprises the steps of:
   (c-1) elongating the first and second viscous compositions for a first predetermined time period;
   (c-2) stopping the elongation for a second predetermined time period; and
   (c-3) further elongating the elongated first and second viscous compositions for a third predetermined time period.

12. The method of claim 11, wherein air is blown in at least one of the steps (c-1) to (c-3).

13. The method of claim 1, wherein the first viscous composition contains at least one first active ingredient that can induce a pharmacological or cosmetic effect when being introduced into a subject and the second viscous composition contains at least one second active ingredient that can induce a pharmacological or cosmetic effect when being introduced into a subject.

14. The method of claim 13, wherein the first active ingredient is different from the second active ingredient and the pharmacological or cosmetic effect induced by the first active ingredient is the same as or different from the pharmacological or cosmetic effect induced by the second active ingredient.

15. The method of claim 1, wherein the first viscous composition, the second viscous composition, or both contain at least one biocompatible material, at least one biodegradable material, or a combination thereof.

16. The method of claim 1, wherein at least a portion of the microstructure contains an active ingredient that can induce a first pharmacological or cosmetic effect when being introduced into a subject and at least one of the other portions of the microstructure contains a different active ingredient that can, when being introduced into a subject, induce a pharmacological or cosmetic effect that is the same as or different from the first pharmacological or cosmetic effect.

17. A method of manufacturing a microstructure, the method comprising the steps of: (a) facing the inner surface of a first substrate with the inner surface of a second substrate, wherein the first substrate has a first viscous composition spotted directly or indirectly on the inner surface of the first substrate at predetermined positions and the second substrate has a second viscous composition spotted directly or indirectly on the inner surface of the second substrate at predetermined positions; (b) moving the first substrate, the second substrate, or both so as to allow the first viscous composition and the second viscous composition to become in contact with each other; (c) moving the first substrate, the second substrate, or both in opposite directions at a first speed so as to allow the first viscous composition and the second viscous composition to elongated; (d) blowing air directly or indirectly to the first and second viscous compositions to solidify the first and second viscous compositions; and (e) moving the first substrate, the second substrate, or both at a second speed higher than the first speed so as to cut the solidified first and second viscous compositions.

\* \* \* \* \*